(12) United States Patent
Sharifzadeh et al.

(10) Patent No.: US 9,814,417 B2
(45) Date of Patent: Nov. 14, 2017

(54) NONINVASIVE MEASUREMENT OF FLAVONOID COMPOUNDS IN BIOLOGICAL TISSUE

(75) Inventors: Mohsen Sharifzadeh, Salt Lake City, UT (US); Igor V. Ermakov, Salt Lake City, UT (US); Werner Gellermann, Salt Lake City, UT (US)

(73) Assignee: Longevity Link Corporation, Salt Lake City, UT (US)

( * ) Notice: Subject to any disclaimer, the term of this patent is extended or adjusted under 35 U.S.C. 154(b) by 1728 days.

(21) Appl. No.: 12/352,702

(22) Filed: Jan. 13, 2009

(65) Prior Publication Data

US 2010/0179435 A1 Jul. 15, 2010

(51) Int. Cl.
*A61B 5/1455* (2006.01)
*A61B 5/145* (2006.01)
*G01N 21/64* (2006.01)

(52) U.S. Cl.
CPC ........ *A61B 5/1455* (2013.01); *A61B 5/14546* (2013.01); *G01N 21/64* (2013.01); *G01N 2021/6421* (2013.01)

(58) Field of Classification Search
CPC ... A61B 5/0059; A61B 5/0071; A61B 5/0075; A61B 5/0082
(Continued)

(56) References Cited

U.S. PATENT DOCUMENTS 5,697,373 A * 12/1997 Richards-Kortum et al. .............................. 600/475
6,159,445 A * 12/2000 Klaveness et al. ............ 424/9.6
(Continued)

FOREIGN PATENT DOCUMENTS

WO 2000078217 A1 12/2000
WO 2003014714 A1 2/2003
WO WO-2009/106524 9/2009

OTHER PUBLICATIONS

Cornard, J. et al., Structural Study of Quercetin by Vibrational and Electronic Spectroscopies Combined with Semiempirical Calculations, *Biospectroscopy*, 3: 183-93, 1997.
(Continued)

*Primary Examiner* — Rochelle Turchen
(74) *Attorney, Agent, or Firm* — Austin Rapp

(57) ABSTRACT

Methods and apparatus are disclosed which facilitate the rapid, noninvasive and quantitative measurement of the concentration of flavonoid compounds, as well as their isomers and metabolites, in biological tissue such as human skin. Low-intensity, visible-light illumination of intact tissue provides for high spatial resolution, and allows for precise quantification of the flavonoid levels in the tissue. The preferred embodiments make use of a previously unknown, low-oscillator strength, optical absorption transition of flavonoids. This makes it possible to optically excite flavonoids in living human tissue outside the absorption range of other, potentially confounding skin chromophores. A system constructed in accordance with the invention includes a source of light for illuminating a localized region of tissue with light that overlaps the absorption bands of a flavonoid compound; a device for detecting the fluorescence emitted by the flavonoid compound resulting from the illumination; and a processor for determining the concentration level of the flavonoid compound based upon the detected fluorescence.

26 Claims, 44 Drawing Sheets

Basics structure of flavonoids

(58) Field of Classification Search
USPC .................................................. 600/473–477
See application file for complete search history.

(56) References Cited

U.S. PATENT DOCUMENTS

| | | | |
|---|---|---|---|
| 6,205,354 | B1 | 3/2001 | Gellermann et al. |
| 6,421,455 | B1 | 7/2002 | Rosen et al. |
| 2004/0130714 | A1 | 7/2004 | Gellerman et al. |
| 2004/0233448 | A1 | 11/2004 | Goulas et al. |
| 2009/0299154 | A1 | 12/2009 | Segman |
| 2009/0306521 | A1* | 12/2009 | Ermakov et al. ............. 600/477 |

OTHER PUBLICATIONS

Cornard, J. et al., Computational and Spectroscopic Characterization of the Molecular and Electronic Structure of the Pb(II)-Quercetin Complex, *The Journal of Physical Chemistry A*, 109: 10044-51, 2005.

Ermakov, I. et al., Resonance Raman detection of carotenoid antioxidants in living human tissue, *Journal of Biomedical Optics*, 10(6): 064028-1-18, Nov./Dec. 2005.

Formica, J. et al., Review of the Biology of Quercetin and Related Bioflavonoids, *Food and Chemical Toxicology*, 33(12): 1061-80, 1995.

Hanneken, A. et al., Flavonoids Protect Human Retinal Pigment Epithelial Cells from Oxidative-Stress-Induced Death, *Investigative Ophthalmology & Visual Science*, 47(7): 3164-3177, Jul. 2006.

Harborne, J. et al., Advances in flavonoid research since 1992, *Phytochemistry*, 55: 481-504, 2000.

Jurasekova, Z. et al., Surface-enhanced Raman scattering of flavonoids, *Journal of Raman Spectroscopy*, 37: 1239-41, 2006.

Lotito, S. et al., Dietary Flavonoids Attenuate Tumor Necrosis Factor a-induced Adhesion Molecule Expression in Human Aortic Endothelial Cells, *Journal of Biological Chemistry*, 281(48): 37102-110, Dec. 1, 2006.

Rice-Evans, C. et al., Structure-Antioxidant Activity Relationships of Flavonoids and Phenolic Acids, *Free Radical Biology & Medicine*, 20(7): 933-956, 1996.

* cited by examiner

Basics structure of flavonoids

| Categories | Molecular Structures | Compounds | Major Food Sources |
|---|---|---|---|
| Flavonols | 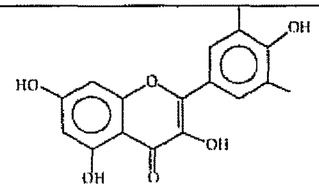 | Quercetin Kaempferol Myricetin | yellow onion, kale, leeks, cherries, broccoli, apples, tea, grapes |
| Flavones | 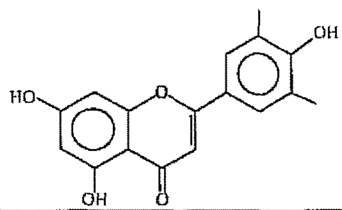 | Apigenin Luteolin Diosmin | parsley, celery, red pepper |
| Flavanones | 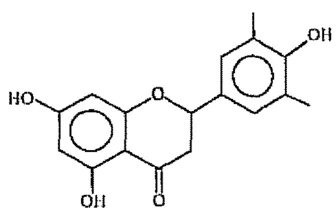 | Naringenin Hesperitin | citrus fruit |
| Catechins | 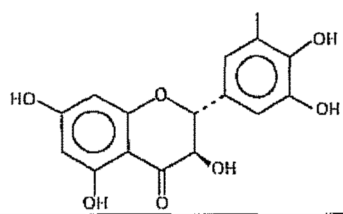 | Catechin Gallocatechin Epigallocatechin | cocoa, beans, apricots, cherries, grapes, peaches, red wine, cider, tea, blackberries |
| Isoflavones | 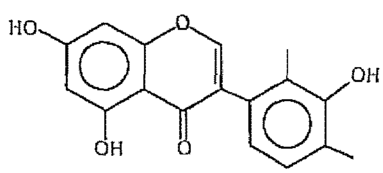 | Genistein | soy beans |
| Anthocyanidins | 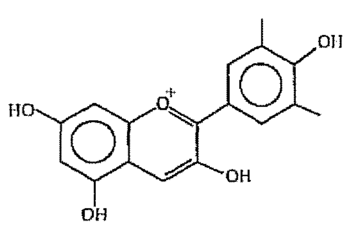 | Pelargonidin | blueberries, black currants, grapes, cherries, rhubarb, plums, strawberries, red wine, red cabbage |

Fig. 2

Reflection spectra of quercetin (a) and kaempferol (b) powder

Absorption spectra of quercetin (a) and kaempferol (b) solutions in methanol; spectra in bottom panel shown on expanded scale Fluorescence spectra of quercetin powder; normalized for same excitation powers Fluorescence of kaempherol powder, normalized for same excitation powers Fluorescence spectra of quercetin, water solution Fluorescence spectra of kaempherol, water solution Reflection spectra of apigenin (a) and luteolin (b) powder Top panel: absorption spectra of apigenin (a) and luteolin (b) methanol solutions (no suspended materials present); Bottom panel: absorption spectrum of apegenin solution on expanded scale Top: Reflection spectrum of diosmin powder
Bottom: Absorption spectra of diosmin in methanol Fluorescence spectra of apigenin powder Fluorescence spectra of luteolin powder Fluorescence spectra of diosmin powder Absorption spectra of hesperidin (a), naringenin (b) powder Top: Absorption spectra of hesperidin (a) and naringenin (b) solutions in methanol Bottom: Absorption spectrum of concentrated solution of naringerin in methanol

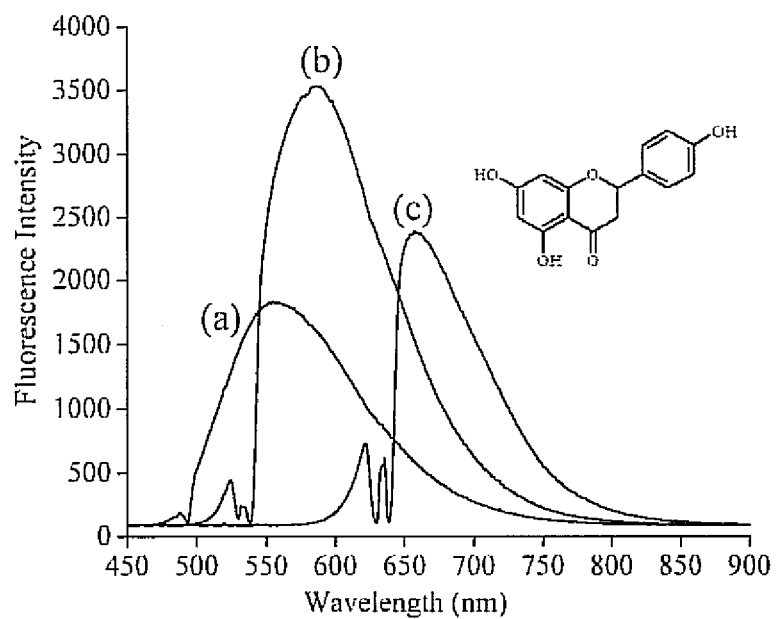
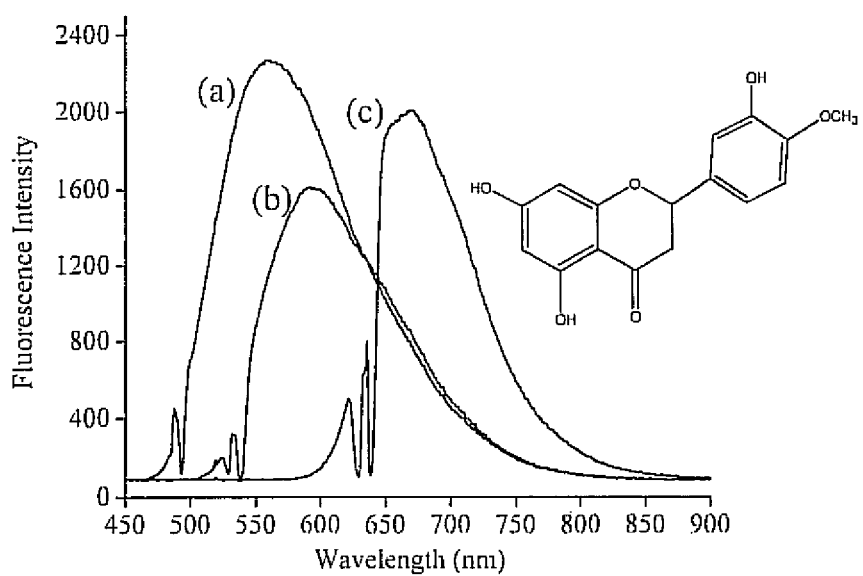
Fig. 18
Fluorescence spectra of narningenin (top) and hesperidin (bottom) powder samples Reflection spectrum of epicatechin powder Abs spectra of catechin (a), epicatechin (b) and gallocatechin (c) solutions in methanol

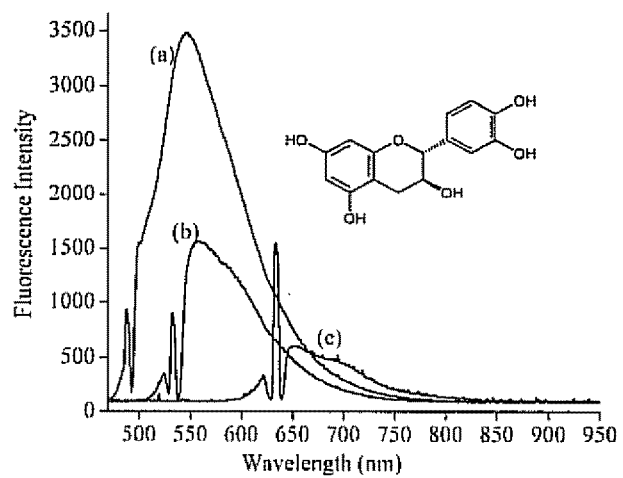
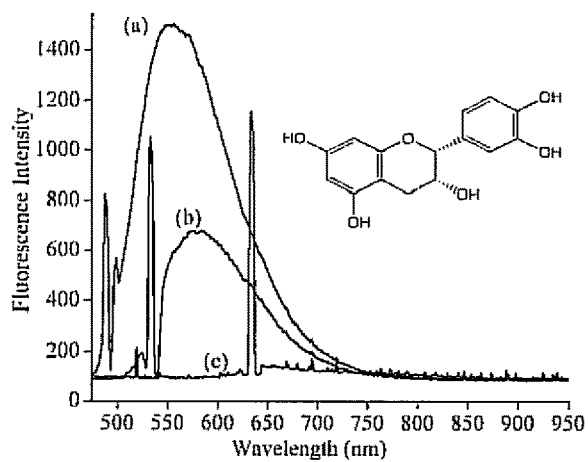
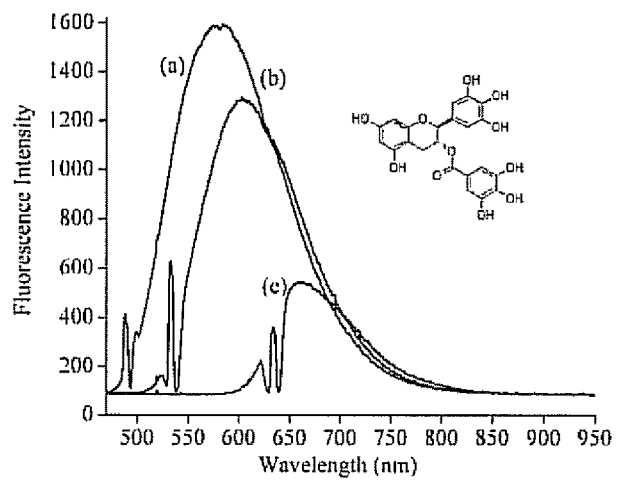
Fig. 21
Fluorescence spectra of catechin (top), epicatechin (b), gallocatechin (bottom) powders Abs spectra of genistein powder (top) and genistein methanol solution (bottom)

Fluorescence spectra of genistein powder

Abs spectrum of pelargonidin chloride powder (top panel) and its solutions in methanol (bottom panel); (a) low concentration, (b) high concentration Fluorescence spectra of pelargonidin powder Normalized fluorescence spectra of flavonoid powders, obtained with 488 nm excitation;
(a) epicatechin, (b) luteolin, (c) diosmin, (d) pelargonidin, (e) catechin, (f) apigenin,
(g) gallocatechin Normalized fluorescence spectra of flavonoid powders obtained with 532 nm excitation; (a) epicatechin, (b) luteolin, (c) diosmin, (d) pelargonidin, (e) catechin, (f) apigenin, (g) gallocatechin Normalized fluorescence spectra of flavonoid powders obtained with 632 nm excitation;
(a) epicatechin, (b) luteolin, (c) diosmin, (d) pelargonidin, (e) catechin, (f) apigenin,
(g) gallocatechin Quercetin bleaching under (a) 532 and (b) 632 excitation; same power levels;
2.5 mm spot size for 532 nm; 1.5 mm spot size for 1.5 mm Linearity of quercetin fluorescence, powder sample Fluorescence spectra of palm tissue site
(same excitation powers; 3 mW)

Fluorescence spectra of detached heel skin tissue sample

Fluorescence spectra of collagen

Fluorescence spectra of quercetin (a) and skin (b), obtained with 632 nm excitation Bleaching kinetics of living skin (a) and quercetin powder (b)

Bottom panel demonstrates the absence of skin fluorescence recovery (at least after 2-min wait), thus revealing a photochemical transformation process causing skin fluorescence bleaching rather then to intersystem conversion....

Bleaching kinetics of living skin (a) 532 nm exc.; (b) 632 nm exc., 2.5 and 1.5 mm spot size, respectively Fluorescence linearity of palm skin tissue site Repeatability measurement for living skin
(632 nm, 1.5 mm spot size)

Fluorescence responses for different tissue sites; index finger (a), thumb (b), forearm (c), palm (d)

Fluorescence in 4 different volunteer subjects

Fluorescence spectra of outer onion layer, measured with blue, green, and red excitation Fluorescence spectra of onion layer (a), quercetin (b), and kaempferol (c)

Fluorescence spectra of green grape (a), red grape (b), and onion layer (c)

Filter-based fluorescence setup

NONINVASIVE MEASUREMENT OF FLAVONOID COMPOUNDS IN BIOLOGICAL TISSUE

FIELD OF THE INVENTION

The present invention relates generally to optical techniques for measuring compounds found in biological tissue. More specifically, the invention relates to a method and apparatus for the noninvasive detection and measurement of levels of flavonoids and related chemical substances in biological tissue, which can be used as a diagnostic aid in assessing antioxidant status and detecting malignancy risk thereof.

BACKGROUND OF THE INVENTION

Flavonoids are ubiquitous, naturally occurring polyphenolic compounds that are often responsible for the bright, attractive colors of plants. Concentrated in numerous fruit, vegetables, berries, grains, roots, stems, and also in beverages like tea, coffee, beer and wine, they are taken up with the diet, and are eventually deposited in the living human tissue cells. Flavonoids have generated enormous interest due to their obvious benefits for human health. One motivator is the explanation of the "French Paradox", which is a surprisingly low cardiovascular mortality rate observed in Mediterranean populations, in spite of the relatively high saturated fat intakes. There is compelling evidence now that certain flavonoids present in red wine, which is consumed in relatively high concentrations along with the fat intakes in Mediterranean diets, are indeed responsible for this effect [1]. Probably based on their common antioxidant function, other kinds of flavonoids present in different food sources appear to have a wide range of beneficial effects as well. They have been associated with the scavenging of free radicals, the prevention of DNA damage, protection from UV-light induced tissue damage, the regulation of good and bad cholesterol levels, clearing of arteries, blocking of tumor growth, the promotion of weight control, protection of retinal pigment epithelial cells from oxidative-stress induced death, etc. [2, 3]. Epidemiological studies consistently show that the consumption of flavonoid-rich food lowers the risk of cancers anywhere from 30 to 75% [2].

The molecular structure common to all flavonoids includes two aromatic benzene rings on either side of a 3-carbon ring skeleton, $C_6$—$C_3$—$C_6$, as illustrated in FIG. 1. Depending on the position of carbon double bonds in the $C_3$ ring, substitution of an OH side group and/or double-bonded oxygen, flavonoids are divided into six main categories. These are flavonols, flavones, flavanones, catechins, isoflavones, and anthocyanidins, all shown in FIG. 2 along with selected representatives and major food sources.

Flavonoid categories with most compounds are flavonols and flavones, both of which have a planar structure due to a double bond in the central $C_3$ ring. The most prominent and probably the most investigated members are quercetin and kaempferol, found in high concentrations in onions, broccoli, apples, and berries. The third flavonoid category, flavanones, is mainly found in citrus fruit. Members of this group are naringenin and hesperetin. A fourth category, catechins, is mainly found in green and black tea and in red wine, while the fifth category, isoflavones, is relatively narrowly distributed in foods, with soy beans being the primary food source. The last category, anthocyanidins, is dominant in cherries, berries, and grapes. Synthesized by plants, flavonoids are often bound to other molecules, such as sugars, in this case forming an inactive glycoside complex. The sugar group is known as the glycone, and the non-sugar group as the aglycone or genin part of the glycoside. As an example, citrus fruit contains hesperidin (a glycoside of the flavanone hesperetin), quercitrin, rutin (two glycosides of the flavonol quercetin), and the flavone tangeritin. In living organisms, like in the human body, enzymes can break up the inactive glycosides if needed, and the sugar and flavonoid components are then made available for use.

Relatively little is known about the energy levels of flavonoids except that the strong electronic absorption transitions connecting these levels occur at relatively high optical energies in the deep WV to blue spectral region. In flavones and flavonols, two characteristic absorption bands have been described in the literature: a "long-wavelength" band in the 300-400 nm region, mostly representing the B-ring absorption, and a "short-wavelength" band in the 240-280 nm region, mostly representing the A-ring absorption. Absorption line shapes and strengths of specific flavonoids are thought to depend on the specific number of hydroxyl groups and/or other substitutions as well on their relative positions [4, 5]. For example, comparing the flavonols quercetin and kaempferol with the flavones luteolin and apigenin, it was found that the two flavonols both have a slightly larger (~30 nm) red shift of their long-wavelength, B-ring, absorption bands relative to those of the two flavone members [6]. This was attributed to the fact that the two flavonols have a hydroxyl group attached to their $C_3$ ring, while the two flavones have no such attachment. For quercetin, the main observed absorption transitions, i.e. those with high oscillator strengths, have been fairly accurately modeled in quantum-chemical configuration interaction calculations, taking into account all excitations from the nine highest occupied molecular orbitals to the nine lowest unoccupied molecular orbitals [7, 8]. The absorption band in the 300-400 nm range is shown to be primarily due to a transition between the highest occupied and lowest unoccupied $\pi$ molecular orbitals, respectively, where the electronic charge density is withdrawn from the B ring to the C=O double bond of the C ring. The transition in the 240-280 nm region is assigned to a transition between the second highest and lowest $\pi$ molecular orbitals, respectively, involving a charge transfer from the region of one aromatic ring through C to the other aromatic ring. No information is given on the existence of energy levels, associated charge distributions, and potential low-energy transitions that could give rise to absorption bands on the long-wavelength side of the B-ring 300-400 nm absorption.

SUMMARY OF THE INVENTION

The present invention is directed methods and apparatus for the noninvasive detection and measurement of flavonoid compounds and related chemical substances in biological tissue. In particular, the invention makes possible the rapid, noninvasive and quantitative measurement of the concentration of flavonoid compounds, as well as their isomers and metabolites, in biological tissue such as human skin. This is accomplished without the requirement of removing tissue or preparing samples for HPLC and mass spectrometry analysis, as required by prior biochemical "gold standard" techniques.

The invention can be used in a direct and quantitative optical diagnostic technique, which uses low-intensity, visible-light illumination of intact tissue, provides for high spatial resolution, and allows for precise quantification of the flavonoid levels in the tissue. Such a technique is useful as a biomarker for fruit and vegetable intake, and it can aid in the detection of tissue abnormalities such as malignancy diseases. The optical detection of flavonoids adds to the optical detection of other antioxidant compounds in tissue, such as the Resonance Raman detection of carotenoids in skin [9], and it may be used in combination with the latter to obtain a more general assessment of bioactive compounds present in the measured living tissues. Examples of biological tissues that can be measured non-invasively with the technique of the invention include human skin and mucosal tissue, bodily fluids such as blood serum, urine, and also plant and fruit tissue samples or extracts.

A noninvasive method of measuring flavonoid levels in biological tissue according to the invention comprises the steps of illuminating a localized region of tissue with light that overlaps the absorption bands of a flavonoid compound; detecting the fluorescence emitted by the flavonoid compound resulting from the illumination; and determining the concentration level of the flavonoid compound based upon the detected fluorescence.

The tissue may be human skin, preferably on a fingertip or other portion of a hand. The concentration level may be used to assess the antioxidant status of the tissue and/or risk or presence of a malignancy or other disease. The light used for excitation is typically in the 300 to 650 nm spectral region, and the fluorescence emitted by the flavonoid may be characterized using fluorescence spectroscopy or an optical detector, particularly if the light is in the red region of the spectrum and the localized region of tissue is substantially melanin-free.

The preferred embodiments make use of a previously unknown, low-oscillator strength, optical absorption transition of flavonoids. This transition manifests itself as a long-wavelength absorption feature that extends far into the visible wavelength range, beyond the well-known 300-400 nm B-ring absorption band. This makes it possible to optically excite flavonoids in living human tissue outside the absorption range of other, potentially confounding skin chromophores. Such chromophores, which include carotenoids, blood, elastin, and collagen, commonly generate unwanted, spectrally overlapping, absorption and/or fluorescence responses under optical excitation of the flavonoid A or B ring absorption bands. However, by exciting the tissue flavonoids in their long-wavelength absorption tail outside the absorption range of these other skin chromophores, the invention makes it possible to generate a fluorescence response from the skin that is only due to the flavonoid molecules present in the optically excited tissue volume. As a consequence, fluorescence spectroscopy may be used as a novel non-invasive, optical, quantitative detection method for flavonoids in human tissue such as skin, and to use this information as an aid in the assessment of flavonoid status and potential disease risk.

A system for measuring flavonoid levels in accordance with the invention includes a source of light for illuminating a localized region of tissue with light that overlaps the absorption bands of a flavonoid compound; a device for detecting the fluorescence emitted by the flavonoid compound resulting from the illumination; and a processor for determining the concentration level of the flavonoid compound based upon the detected fluorescence.

BRIEF DESCRIPTION OF THE DRAWINGS

In order to illustrate the manner in which the above recited and other advantages and objectives of the invention are obtained, a more particular description of the invention briefly described above will be rendered by the reference to specific embodiments thereof, which are illustrated in the appended drawings. Understanding that these drawings depict only typical embodiments of the invention and are not therefore to be considered limiting in scope, the invention will be described and explained with additional specificity and detail through the use of the accompanying drawings in which:

FIG. 2 illustrates the six distinct categories of flavonoids, their molecular structure, and their main food sources;

FIG. 18 shows fluorescence spectra of naringenin and hesperidin crystal powder samples;

FIG. 21 shows fluorescence spectra of catechin, epicatechin, and gallocatechin crystal powder samples at blue, green, and red excitation wavelengths;

DETAILED DESCRIPTION OF THE INVENTION

The present invention uses fluorescence to identify and quantify the presence of flavonoids and similar substances in biological tissue such as skin. In this technique, light is directed onto the tissue, and the fluorescence emitted from the tissue is filtered and detected. The fluorescence intensity can be used as an indicator for the concentration of the flavonoids present in a subject's skin, since the fluorescence intensity can be expected to scale linearly with the concentration of the flavonoids present in the excited tissue volume. A preferred embodiment uses tissue sites such as the palm of the hand that is held against an optical window. The apparatus allows one to continuously measure and display the intensity of the fluorescence. The total time it takes to assess a subject's skin flavonoid level is very brief amounting to only a few seconds.

In a method for the noninvasive measurement of flavonoids and related chemical substances in biological tissue according to the current invention, a light source such as a tungsten-halogen lamp, a light emitting diode, or a laser is used, any of which feature light emission with sufficiently high intensity at spectral locations in the wavelength range where absorption bands of the flavonoid compounds occur, i.e. in the 300 to 650 nm spectral region. The fluorescence intensity emitted from the skin flavonoids is proportional to their concentration in the excited tissue volume. Therefore, the fluorescence intensity of the skin flavonoids can be used as an optical measure for the skin flavonoid concentration, and this information can be used to assess the flavonoids antioxidant status of the tissue. The concentration levels can be compared with levels of normal biological tissue to assess the risk or presence of a malignancy disease.

Figure 1:
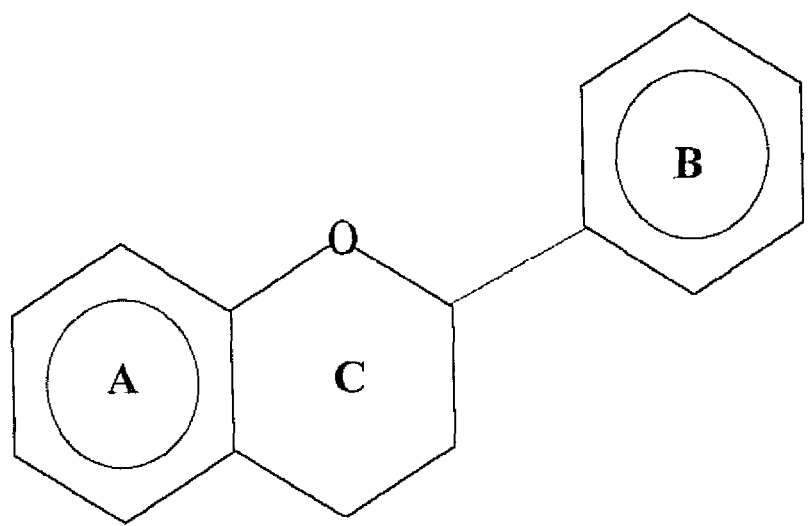
FIG. 1 illustrates the basic molecular structure of all flavonoids.
Figure 7:
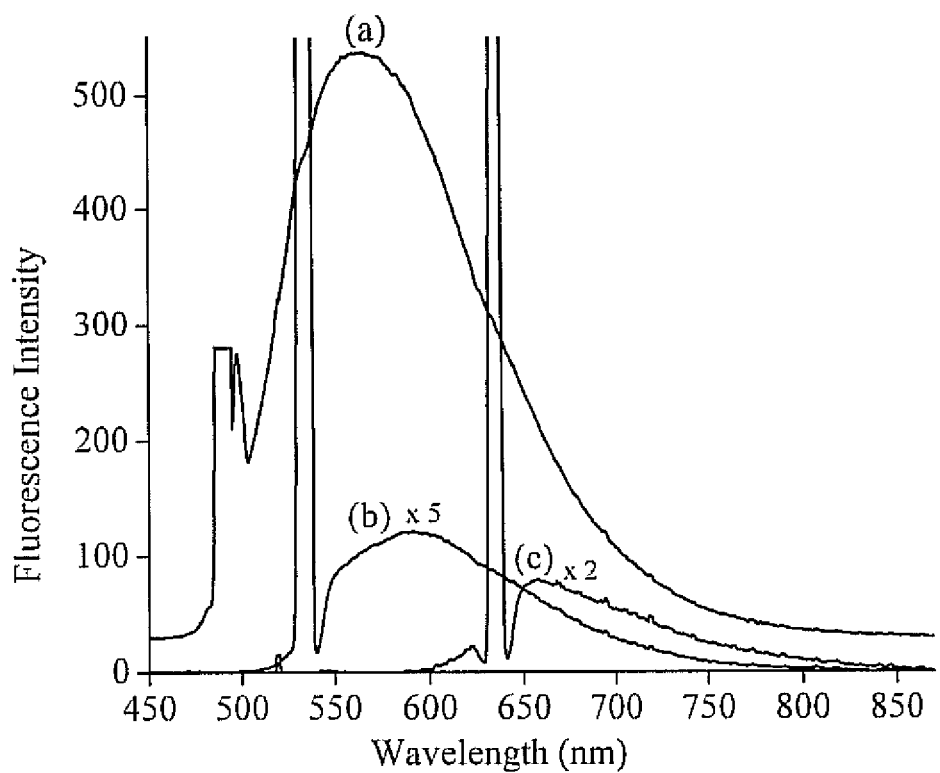
FIG. 7 shows fluorescence spectra of kaempherol crystal powder at blue, green, and red excitation wavelengths.

FIG. 1 shows schematically the molecular structure that is common to all flavonoids. It consists of a central ring with three carbon atoms that is connected on either side with an aromatic benzene ring. FIG. 7 shows the main categories of flavonoids, their molecular structure, main members of the various categories and their main food sources. Individual flavonoids differ in the number and position of hydroxyl molecules attached at various carbon sites, as well as the existence and positioning of carbon double bonds in the central ring.

Figure 3:
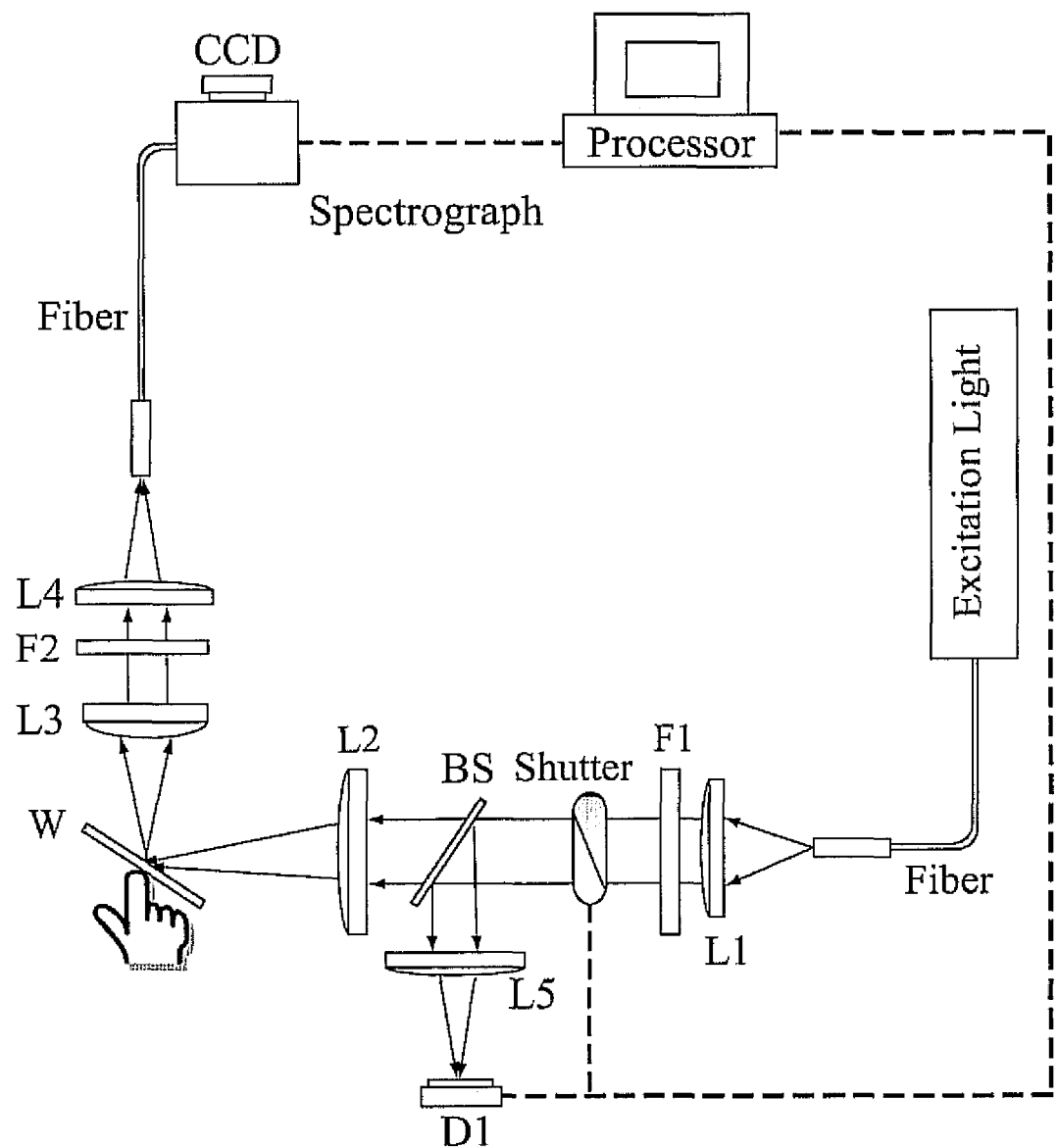
FIG. 3 is a general schematic depiction of the apparatus according to the present invention that measures the emission spectra of flavonoids in a variety of samples, including human skin tissue sites.

FIG. 3 is a general schematic depiction of the apparatus of the present invention for measuring the emission spectra of flavonoids and like substances in biological tissue using fluorescence spectroscopy. The apparatus contains a light source, which in one preferred embodiment of the invention is a light emitting diode, emitting light with ~20 nm bandwidth centered at 627 nm. Alternatively, the light source may comprise other devices for generating light in the spectral range of the flavonoid absorptions. Preferably, in the case of flavonoids, the light source generates light with sufficient intensity at discrete wavelength locations or at certain spectral ranges in the wavelength range 300-650 nm, which overlap with the absorption bands of flavonoid compounds. Such light is readily available, e.g., from commercially produced inexpensive slide projector lamps that are suitable filtered, from light emitting diodes, or from lasers.

The excitation light source is in optical communication with a light beam delivery and collection system that can include various optical components for directing the excitation light to the tissue or sample to be measured and collecting the emitted fluorescence. As shown in FIG. 3, the optical components of the apparatus include the light source, a mechanical shutter, a beam splitter that sends part of the excitation light to a monitoring detector, a beam expander, a filter, a lens, a window that is placed against the tissue or sample to be measured, a light collection lens, a filter, a beam contractor, a light collection fiber, a spectrograph, a fluorescence detector, and a computer processor/monitor. The interaction of these optical components with the light from the light source will be discussed in further detail below.

The detection part of the apparatus can contain a spectrograph or spectrometer, which serves to spectrally disperse the light components of the flavonoid fluorescence. The spectrally dispersive system can be replaced by various alternative optical components such as diffraction gratings, prisms, holographic filters, dielectric filters, combinations thereof, and the like.

The spectrally selective system is in optical communication with a detection means such as a light detection system, which is capable of measuring the intensity of the emitted fluorescence as a function of wavelength in the wavelength range of interest, such as the wavelength range characteristic for the flavonoid compounds in human skin. The detection system may comprise, but is not limited to, devices such as a CCD (charge-coupled device) detector array, an intensified CCD detector array, a photomultiplier apparatus, photodiodes, or the like.

The spectrally selective system and light detection system can be selected from commercial spectrometer systems such as a low-resolution grating spectrometer employing rapid detection with a charge-coupled silicon detector array. For example, a grating spectrometer can be used which employs a dispersion grating with 300 lines/mm, and a silicon detector array with 14 µm individual pixel width. Another suitable spectrometer is a holographic imaging spectrometer, which is interfaced with a CCD detector array, and employs a volume holographic transmission grating. The spectrally selective system and light detection system can also be combined into an imaging system that includes spectrally selective optical elements used in association with a low light level CCD imaging array such as an intensified CCD camera.

The detected light is preferably converted by a light detection system into a signal that can be visually displayed on an output display such as a computer monitor or the like. It should be understood that the light detection system can also convert the light signal into other digital or numerical formats, if desired. The resulting emitted fluorescence light signals are preferably analyzed via a quantification means such as a quantifying system, which may be calibrated by comparison with chemically measured flavonoid levels from other experiments. The quantifying means may be a computer, preferably one in which data acquisition software is installed that is capable of spectral manipulations, such as the normalization of the spectra to an emission standard, and the determination of concentration values of the flavonoids present in the measured tissue volume. The quantifying system may also comprise a CCD image display or monitor. The quantifying system may be combined with the output display in one computer and can calibrate the results with flavonoid levels obtained with other experiments such as the optical density that is proportional to actual flavonoid levels.

During operation of the apparatus, a light beam is generated from the light source and is directed through an input optical fiber to the delivery system. Alternatively, the light beam is directed to the light delivery system with the help of mirrors. Part of the excitation light routed toward the system is split off with a beam splitter to monitor its intensity, and the remainder is expanded, filtered, and imaged with a lens through a window onto the sample or tissue volume to be measured. The latter is in contact with the window. The fluorescence emitted from the sample or skin is collected by a lens, and is imaged onto the face of an output fiber that routes the light to a spectrally selective system such as a grating spectrograph. The spectrally dispersed light is directed to a light detection system that measures the light intensity as a function of wavelength in the wavelength range spanning the fluorescence range of all skin flavonoids. Alternatively, the spectrally selective system is skipped, and the fluorescence is routed directly to a light detection system. The light detection system then converts the emitted fluorescence signals into a form suitable for visual display such as on a computer monitor or the like, and the resulting flavonoid emission is analyzed with the quantification system.

The present invention is particularly useful for the detection of flavonoid content in living human tissue. Humans ingest significant amounts of flavonoids in their diet. After uptake by the human body, they have the ability to modify the body's reaction to allergens, viruses, and carcinogens. They are thought to exhibit anti-allergic, anti-inflamatory, anti-microbial and anti-cancer activity. There is strong interest in flavonoids in the food and nutritional supplement industry due to their medicinal properties, especially their potential role in the prevention of cancers and cardiovascular disease. Evidently, the beneficial effects of fruit and vegetables and tea or even red wine can be attributed to a large extent to the inherent flavonoids rather than other compounds. In many cases, specific biochemical and physiological actions have been suggested for the flavonoid compounds. For example, kaempferol has been shown to revert the transformed phenotype of phorbol ester-treated mouse fibroblasts or v-H-ras-transformed NIH 3T3 cells. Another example, apigenin, has been found to inhibit cell proliferation by arresting the cell cycle at the $G_2/M$ phase. Inhibition of growth through cell cycle arrest and induction of apoptosis appear to be related to induction of p53. Inhibitory effects on tumor promotion may also be due to inhibition of kinase activity and the resulting suppression of oncogene expression. It has also been reported to inhibit topoisomerase I catalyzed DNA religation and to enhance gap junctional intercellular communication. A third example, gallocatechin, has been suggested to inhibit the growth and adherence of *P. gingivalis* onto the buccal epithelial cells. A fourth example, genistein, has been shown to be an inhibitor of tyrosine protein kinase, a competitive inhibitor of ATP in other protein kinase reactions, and an antiangiogenic agent, down-regulating the transcription of genes involved in controlling angiogenesis.

While the microscopic mechanisms of their medicinal benefits are still subject of investigation [10], it is clear that a noninvasive detection method for flavonoids in living human tissue would provide a strong advantage. Current detection methods require mass spectrometry and liquid chromatography methods and as invasive methods are applicable only to biopsied tissue samples and bodily fluids. Noninvasive optical detection, in contrast, allows in-situ measurements of undisturbed living human tissue, provide rapid assessment of flavonoid status, serve as biomarker for fruit and vegetable uptake in epidemiological studies, and provide a convenient means for monitoring flavonoid uptake upon dietary modifications and nutritional supplementation Various experiments were performed which demonstrate that strong flavonoid fluorescence signals are readily obtainable for various areas of the living human skin using safe light exposure levels. The following examples set forth the apparatus and procedures utilized in these experiments as well as the results derived from them.

Example 1

In order to investigate the potential excitation wavelengths useful for the generation of characteristic flavonoid fluorescence signals, we first measured the absorption characteristics of representative compounds. Crystal powder samples with highest possible purity were obtained from Sigma-Aldrich, Inc. They included quercetin dihydrate and kaempferol for flavonol examples, apigenin, luteolin, and diosmin rutinoside for flavone examples, naringenin and hesperidin (rhamnoglucoside of hesperitin) for flavanones, the catechins gallocatechin and epicatechin, the isoflavone genistein, and the anthocyanidin compound pelargonidin chloride. The manufacturer lists the following synonyms for some of the measured flavonoid compounds.

For kaempferol: 3,4',5,7-Tetrahydroxyflavone, 3,5,7-Trihydroxy-2-(4-hydroxyphenyl)-4H-1-benzopyran-4-one, Robigenin;

for apigenin: 4',5,7-Trihydroxyflavone;

for luteolin: 3',4',5,7-Tetrahydroxyflavone;

for diosmin: 3',5,7-Trihydroxy-4'-methoxyflavone 7-rutinoside;

for naringenin: 4',5,7-Trihydroxyflavanone, (±)-2,3-Dihydro-5,7-dihydroxy-2-(4-hydroxyphenyl)-4H-1-benzopyran-4-one;

for hesperedin: Hesperetin 7-rhamnoglucoside, Hesperitin-7-rutinoside;

for catechin: (2S,3R)-2-(3,4-Dihydroxyphenyl)-3,4-dihydro-1(2H)-benzopyran-3,5,7-triol, (−)-trans-3,3',4',5,7-Pentahydroxyflavane;

for gallocatechin: (2S,3R)-2-(3,4,5-Trihydroxyphenyl)-3,4-dihydro-1(2H)-benzopyran-3,5,7-triol;

for epicatechin: (−)-cis-3,3',4',5,7-Pentahydroxyflavane, (2R,3R)-2-(3,4-Dihydroxyphenyl)-3,4-dihydro-1(2H)-benzopyran-3,5,7-triol;

for genistein: 4',5,7-Trihydroxyisoflavone, 5,7-Dihydroxy-3-(4-hydroxyphenyl)-4H-1-benzopyran-4-one;

for pelargordinin chloride: 3,4',5,7-Tetrahydroxyflavylium chloride.

For each compound we determined the absorption characteristics of samples in crystal powder form, using white-light reflection spectroscopy. Experimental details of the method can be found in pending patent application Ser. No. 12/134,667, the entire content of which is incorporated herein by reference. For solutions of the compounds we used a Perkin-Elmer UV/VIS/NIR absorption spectrophotometer.

Figure 4:
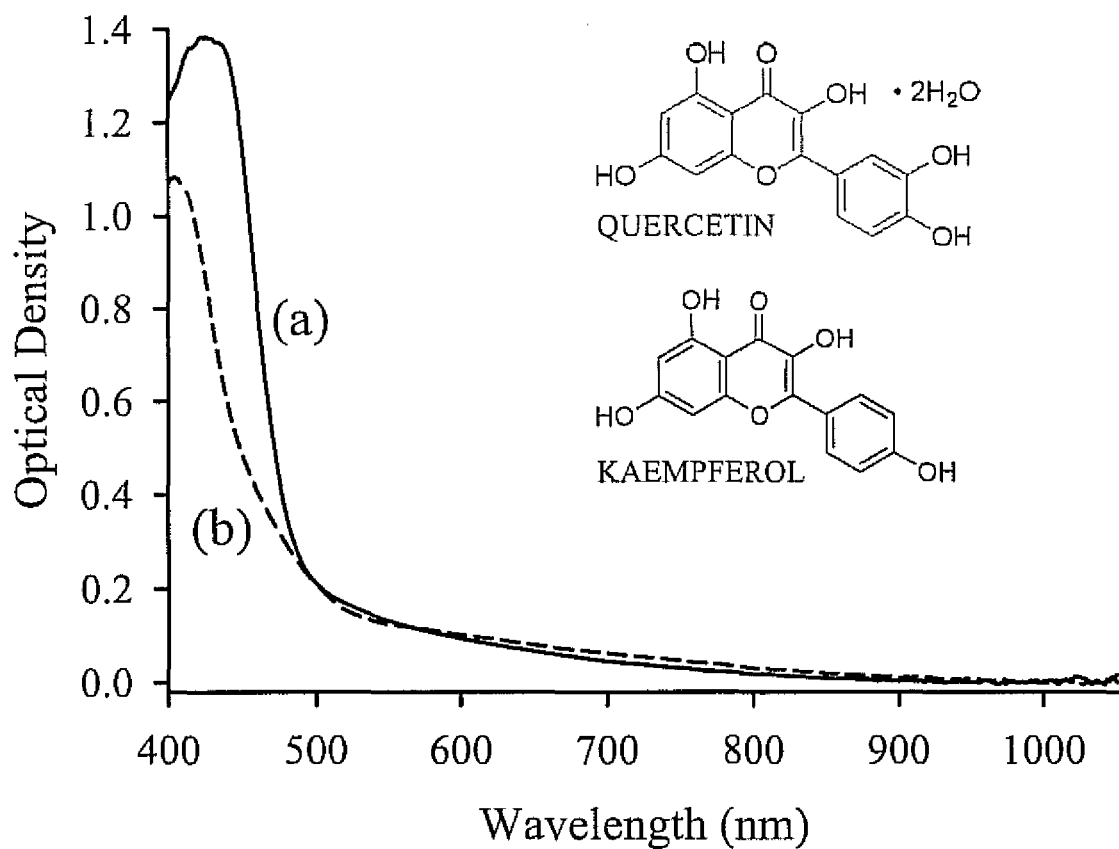
FIG. 4 shows absorption spectra of pure quercetin and kaempferol crystal powder samples.
Figure 5:
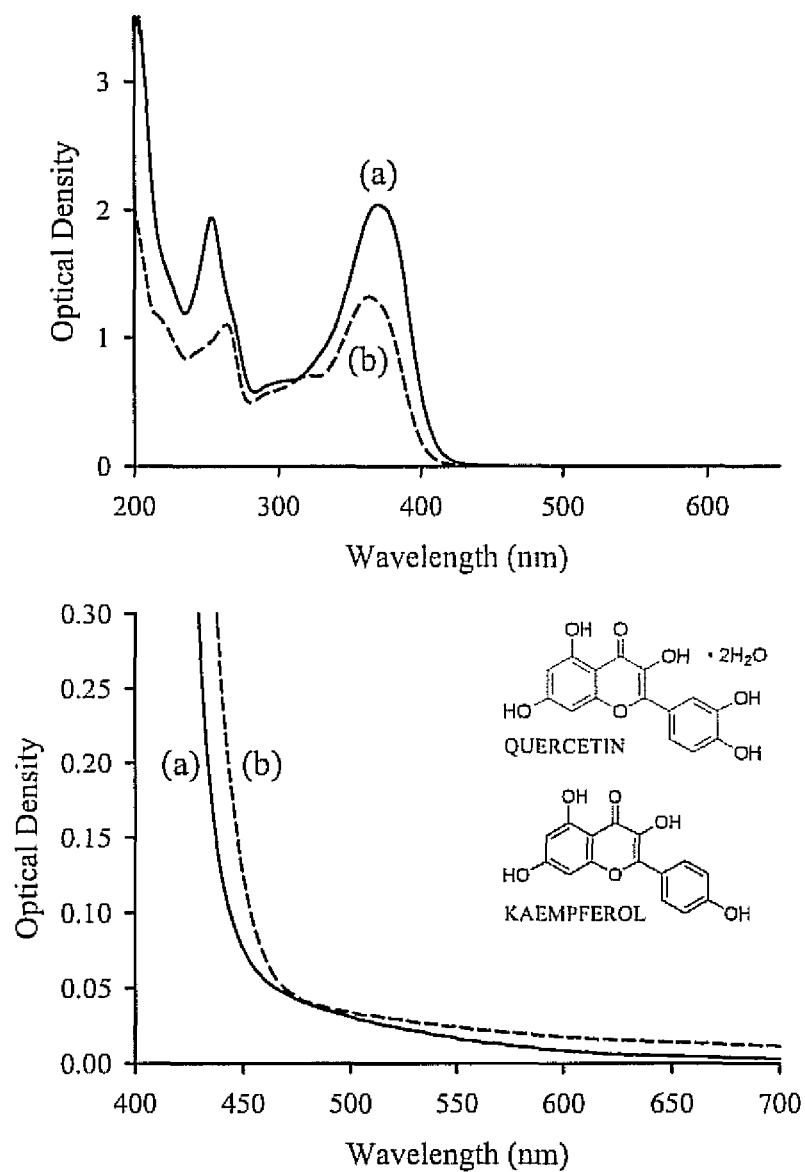
FIG. 5 shows absorption spectra of methanol solutions of quercetin and kaempherol.

In FIGS. 4 and 5, we show the absorption results for the flavonol compounds quercetin and kaempferol. The absorption bands are very similar and feature prominent broad bands peaking in the 400 to 430 nm range. Importantly, they also feature a weak, but clearly noticeable long wavelength absorption tail in the visible/far-red wavelength region, extending from about 500 to 800 nm. This weak, long-wavelength tail is not only visible for these flavonol compounds in powder form, which could point to a scattering effect, but also for methanol solutions. The absorption spectra obtained for perfectly clear methanol solutions of quercetin and kaempferol, i.e. solutions having no residual suspended flavonol material, are shown in the top panel of FIG. 5, where trace (a) belongs to quercetin and trace (b) to kaempferol. The spectra reveal the well-known, three-band absorption pattern of flavonoid solutions in the deep UV/blue spectral region, characterized by strong optical absorption transitions with maxima near ~200 nm, 260 nm, and 380 nm in the case of the two flavonol solutions. Compared to the solid-state form, the long-wavelength absorption bands of the compounds in solution are shifted slightly (several ten nm) to shorter wavelengths. Importantly, when measuring the absorption behavior of the more concentrated solutions in the visible wavelength region, a weak but clearly recognizable absorption tail of the two flavonols is apparent again, stretching up to wavelengths well into the visible/red wavelength region (up to about 650 nm).

Figure 6:
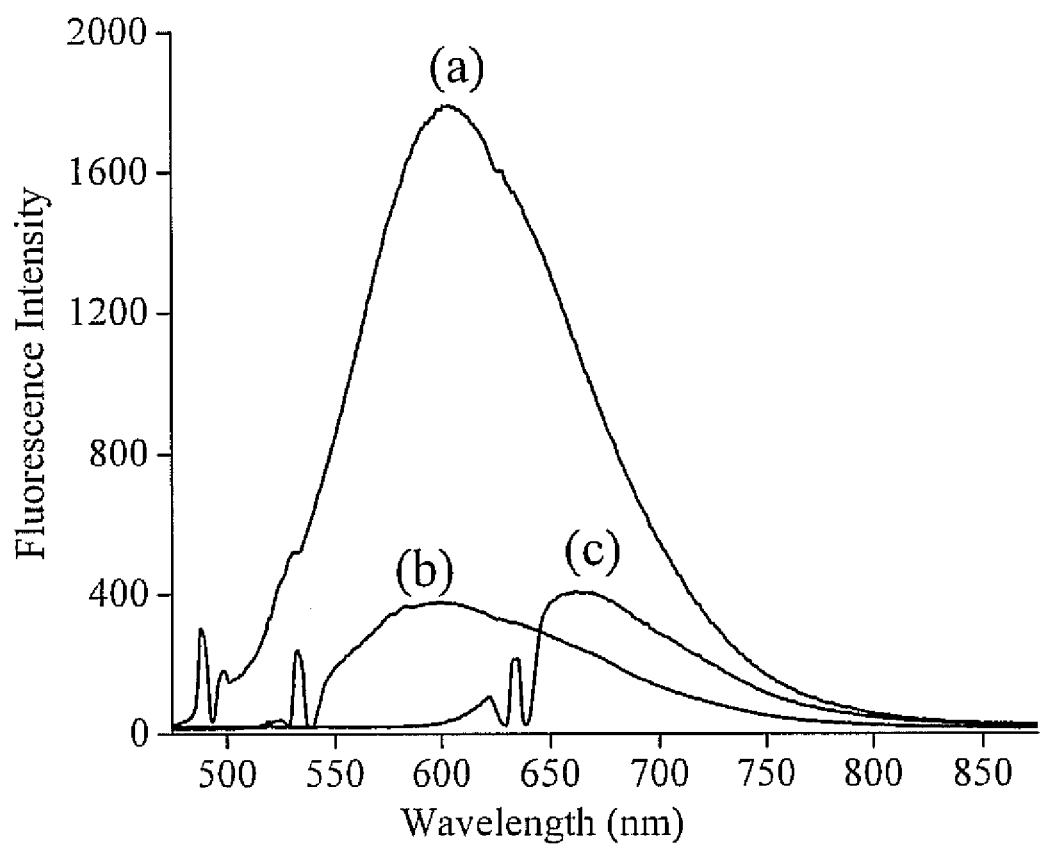
FIG. 6 shows fluorescence spectra of quercetin crystal powder at blue, green, and red excitation wavelengths.

Next, using the experimental apparatus of FIG. 3, we measured the emission behavior of both flavonol compounds. As excitation light wavelengths we tested 488, 532, and 632 nm, all exciting the absorption band on the long wavelength shoulder. The results for a quercetin powder sample are shown in FIG. 6. They reveal that for all three excitation wavelengths, a strong fluorescence response is obtained. At 488 nm excitation, which has the strongest overlap with the absorption, a very broad fluorescence band is obtained, with maximum at ~600 nm, halfwidth of ~150 nm, and measurable fluorescence intensity extending up to about 800 nm in the near infrared region. The sharp peak at 488 nm is an artifact due to leakage of the excitation light into the spectrometer. Under 532 nm excitation, the emission occurs again with a maximum at ~600 nm, slightly reduced halfwidth, and strength that is reduced by a factor of five due to the reduced overlap of the excitation with the absorption band. At 632 nm excitation, the fluorescence occurs shifted to a position of the maximum near ~670 nm. This shift appears due to the chopped off short-wavelength emission response. However, due to the fluorescence nature of the emission, the obtainable signal strengths are still relatively large, even under these "extreme" excitation conditions. The Stokes shift between long-wavelength absorption and obtained emission is very small, indicating that the emission originates from the same energy state reached in absorption, and thus suggesting that the oscillator strength of the emission is comparable to that of the absorption transition.

In FIG. 7, the emission behavior is shown for kaempferol under the same three excitation conditions. Compared to quercetin, all effects are very similar except the emission maxima for 488 and 532 nm excitation are shifted slightly (by ~40 nm) to shorter wavelengths. Again, the emission range is very large, extending to about 775 nm in the near infrared. Compared to excitation at 488 and 532 nm, the fluorescence intensities obtained with 632 nm excitation are reduced by about one order of magnitude.

Figure 8:
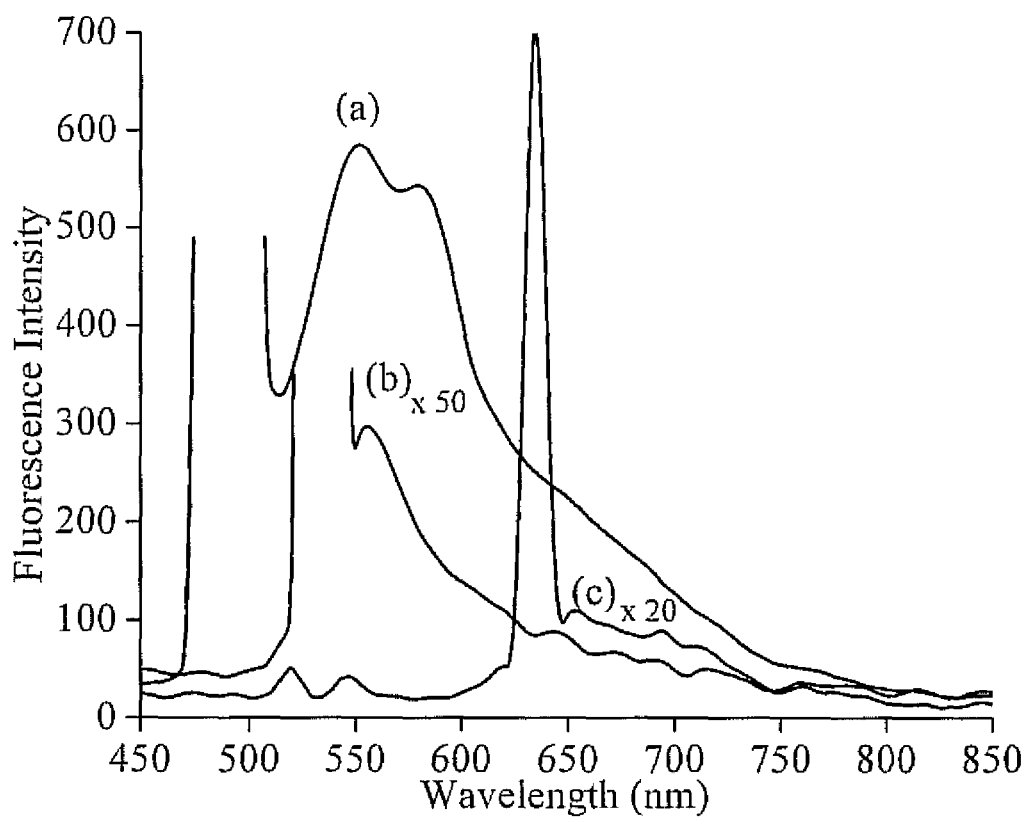
FIG. 8 shows fluorescence spectra of a water solution of quercetin at blue, green, and red excitation wavelengths.
Figure 9:
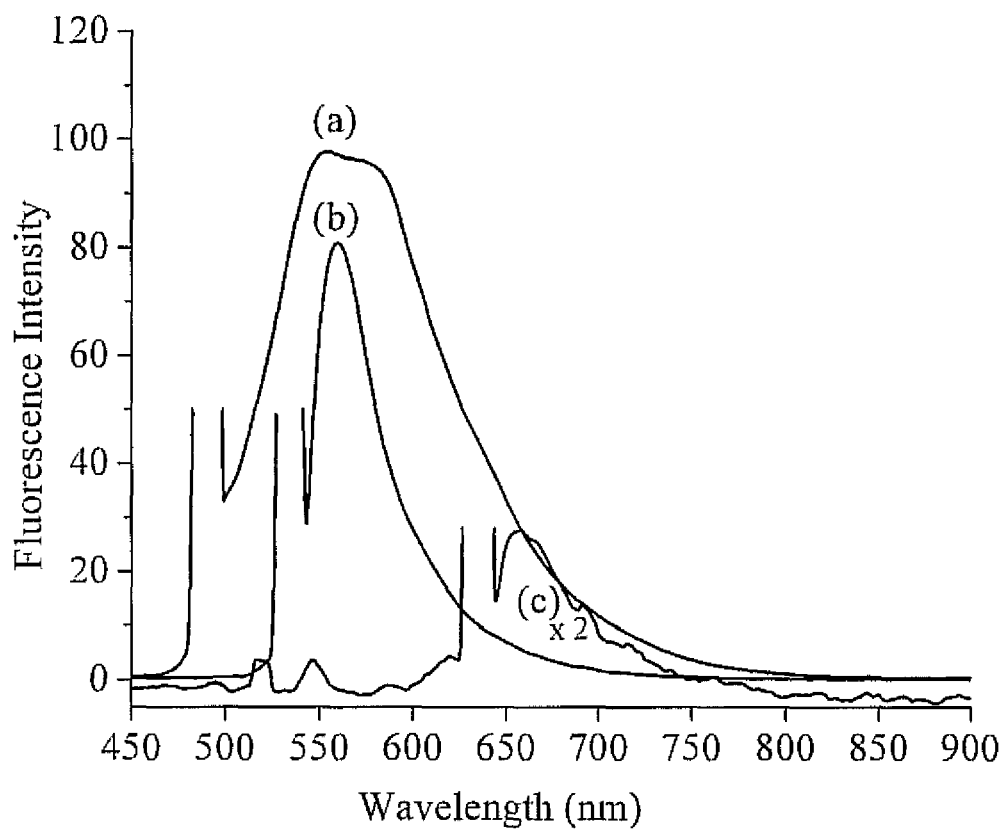
FIG. 9 shows fluorescence spectra of a water solution of kaempherol at blue, green, and red excitation wavelengths.
Figure 10:
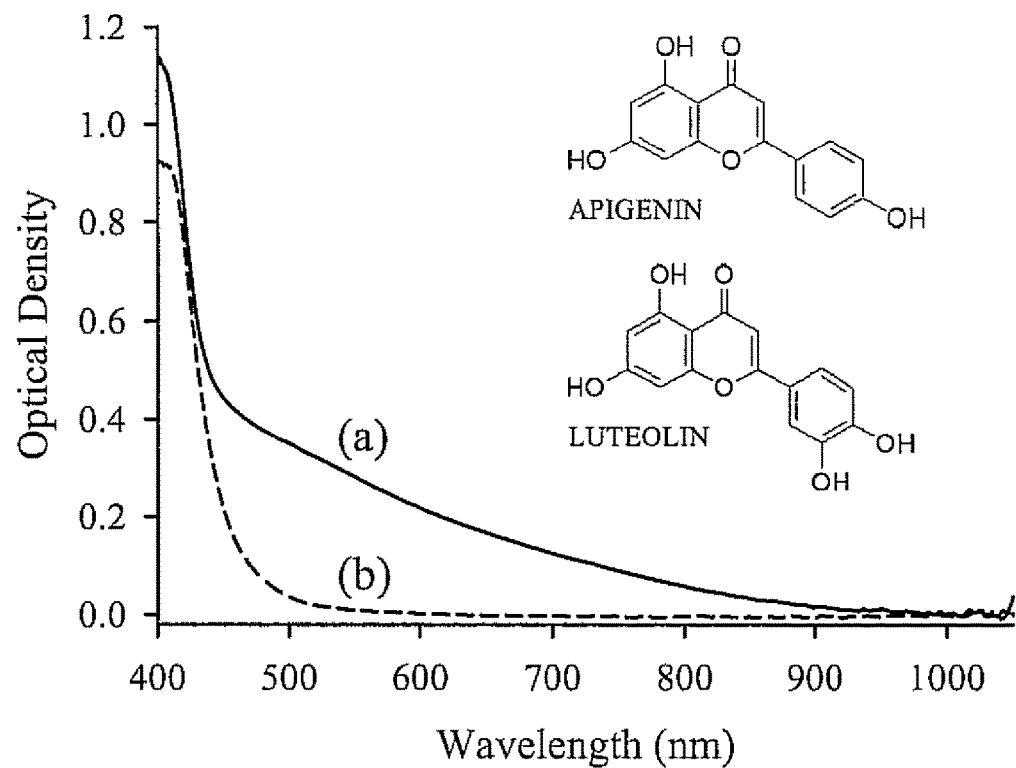
FIG. 10 shows absorption spectra of pure apigenin and luteolin crystal powder samples.
Figure 11:
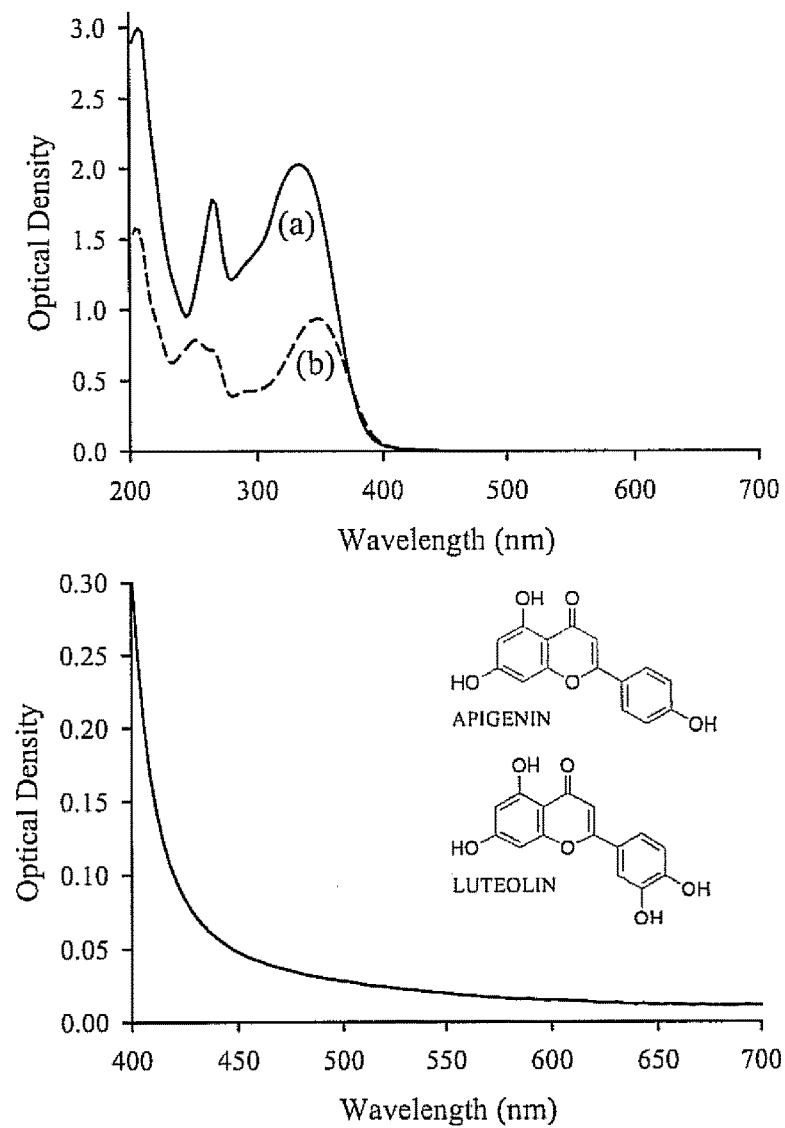
FIG. 11 shows absorption spectra of methanol solutions of apigenin and luteolin.
Figure 12:
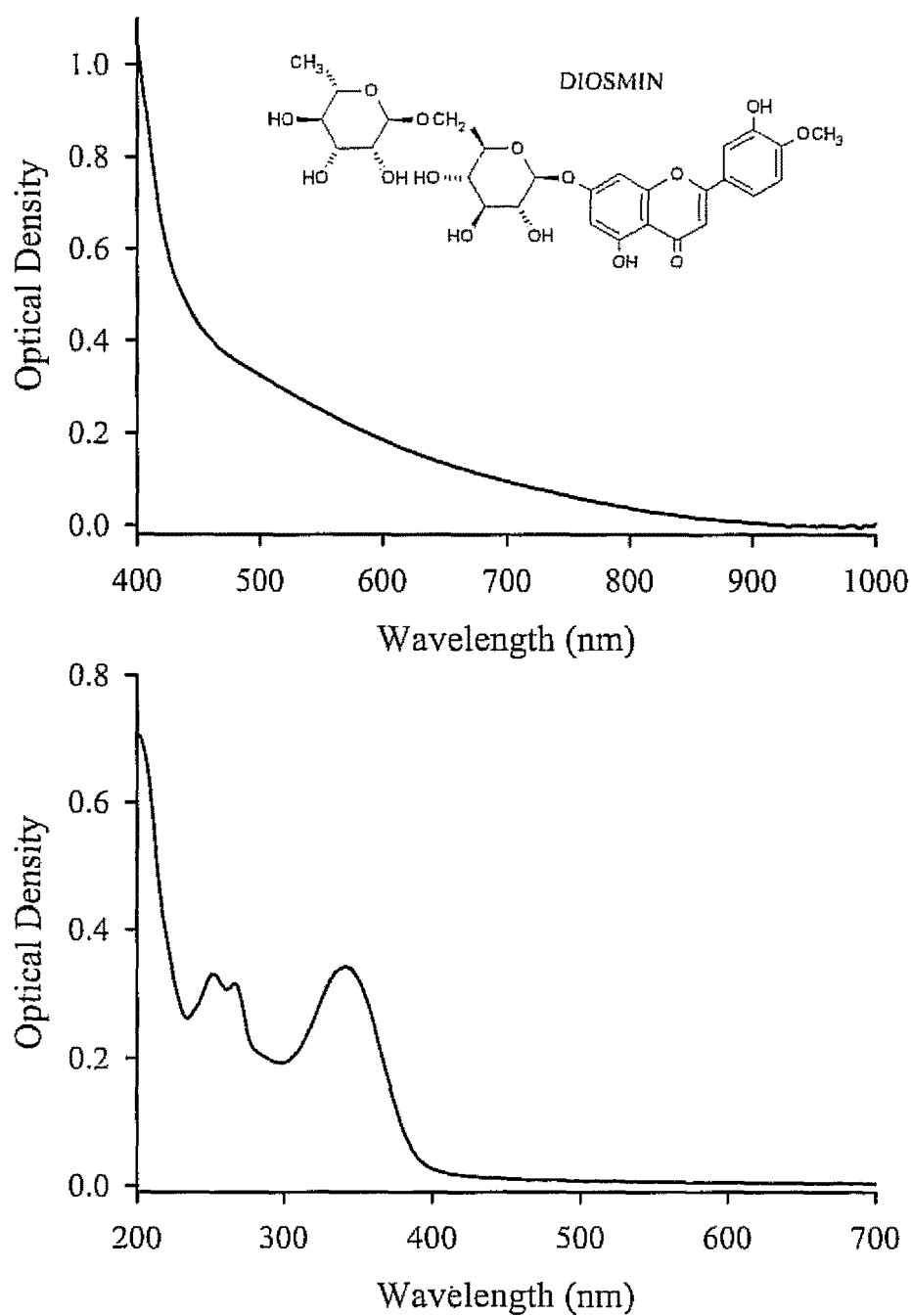
FIG. 12 shows absorption spectra of diosmin crystal powder and methanol solution.

In FIGS. 8 and 9, the emission behaviors are shown, respectively, for aqueous solutions of quercetin and kaempherol. All signal strengths are weaker compared to the powder samples due to the reduced concentration of the active molecules and there is stronger scattering of the excitation light into the spectrometer, as evidenced by the strong, out-of-scale intensities at the excitation wavelengths. Importantly, however, in both cases the emission behavior is very similar again in terms of spectral shapes and locations of the maxima with respect to the pure powder samples.

In FIGS. 10-25 we show absorption and emission results for representative compounds of all other remaining flavonoid categories. In each case, we observe a distinct, long-wavelength absorption tail for the compound in powder form as well as in solution. Also, in each case we obtain again the distinct fluorescence pattern for blue, green, and red excitation, i.e. strong, broad-band fluorescence responses in the 600-800 nm region at each excitation wavelength, with slightly reducing bandwidths upon increasing excitation wavelength.

Figure 13:
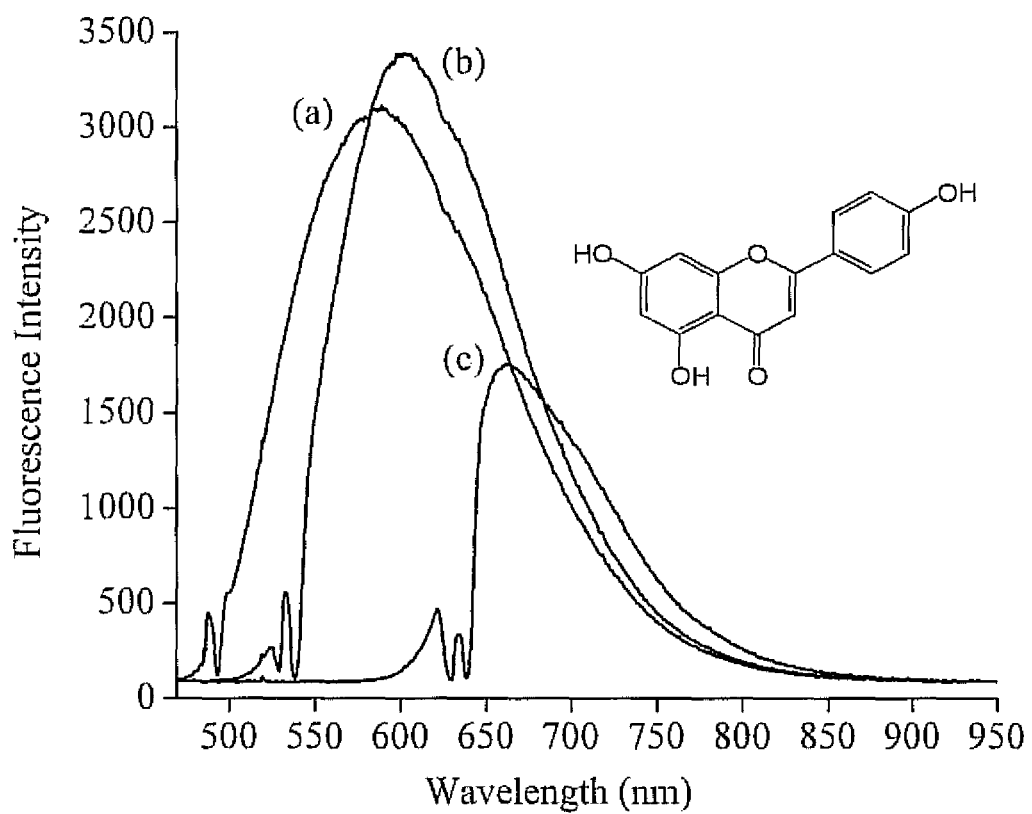
FIG. 13 shows fluorescence spectra of apigenin crystal powder at blue, green, and red excitation wavelengths.
Figure 14:
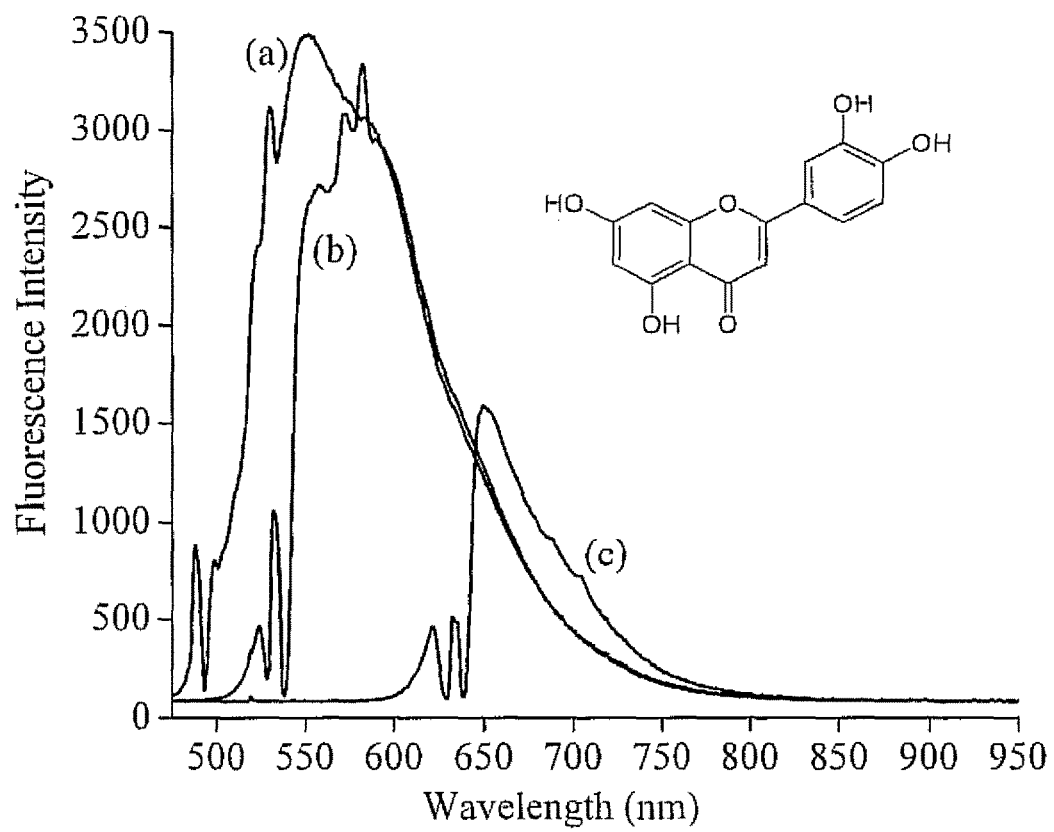
FIG. 14 shows fluorescence spectra of luteolin crystal powder at blue, green, and red excitation wavelengths.
Figure 15:
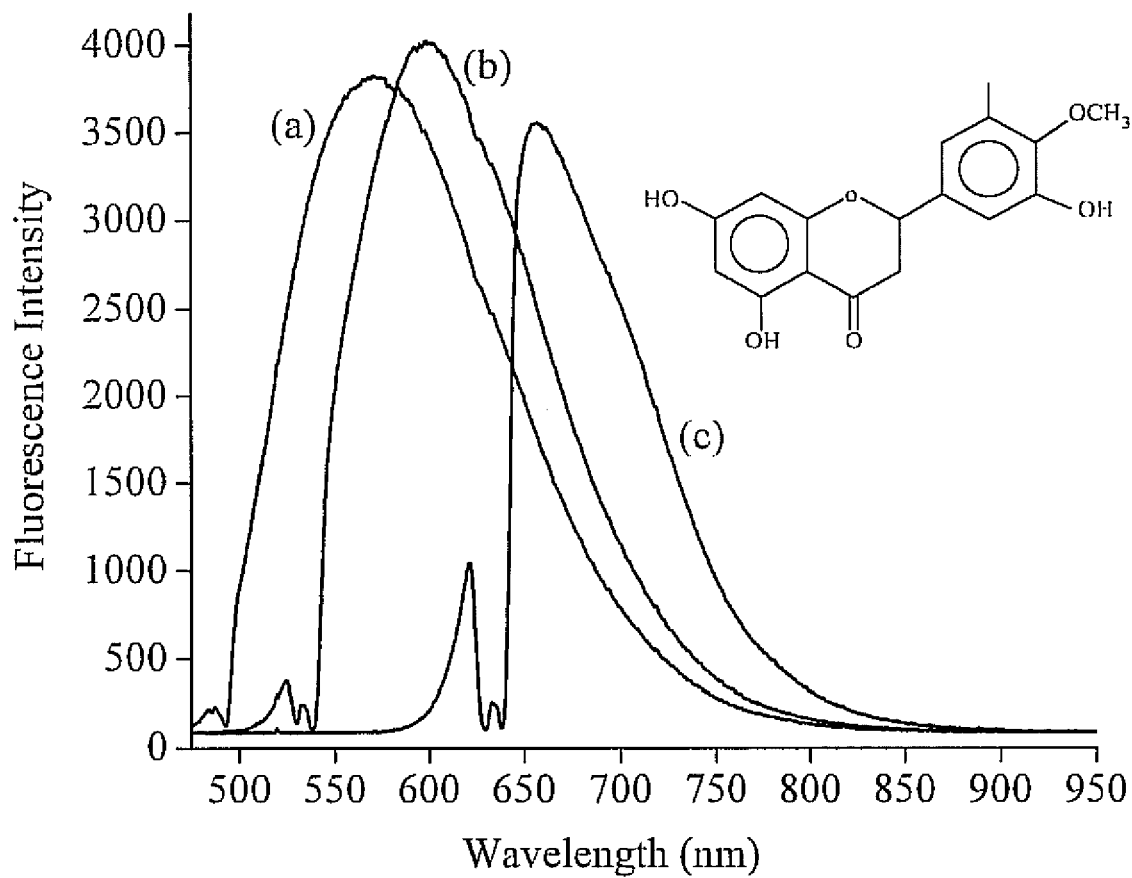
FIG. 15 shows fluorescence spectra of diosmin at blue, green, and red excitation wavelengths.

The absorption and fluorescence properties of the flavones are illustrated in FIGS. 10-15 for the compounds apigenin, luteolin, and diosmin. In apigenin powder, the absorption tail is more prominent than in luteolin, as is apparent from FIG. 10. However, in all cases the absorption tail can be observed with increased-concentration absorption measurements, even in methanol solutions, as is evident from FIGS. 11 and 12. The fluorescence spectra of the three flavone compounds, shown in FIGS. 13-15, are very similar under blue, green, and red excitation, differing slightly with regards to their relative intensities, but importantly, high fluorescence intensities in the 660 nm range are obtainable for all three compounds using long-wavelength excitation at 632 nm.

Figure 16:
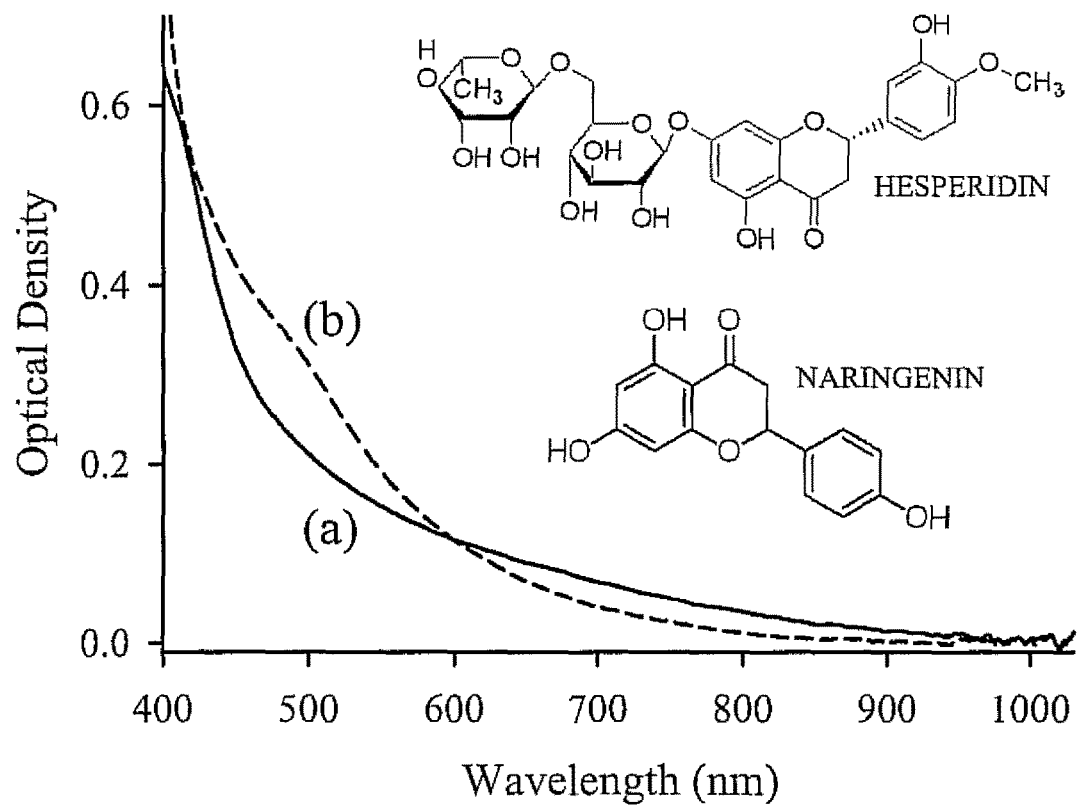
FIG. 16 shows absorption spectra of hesperidin and naringenin crystal powder samples.
Figure 17:
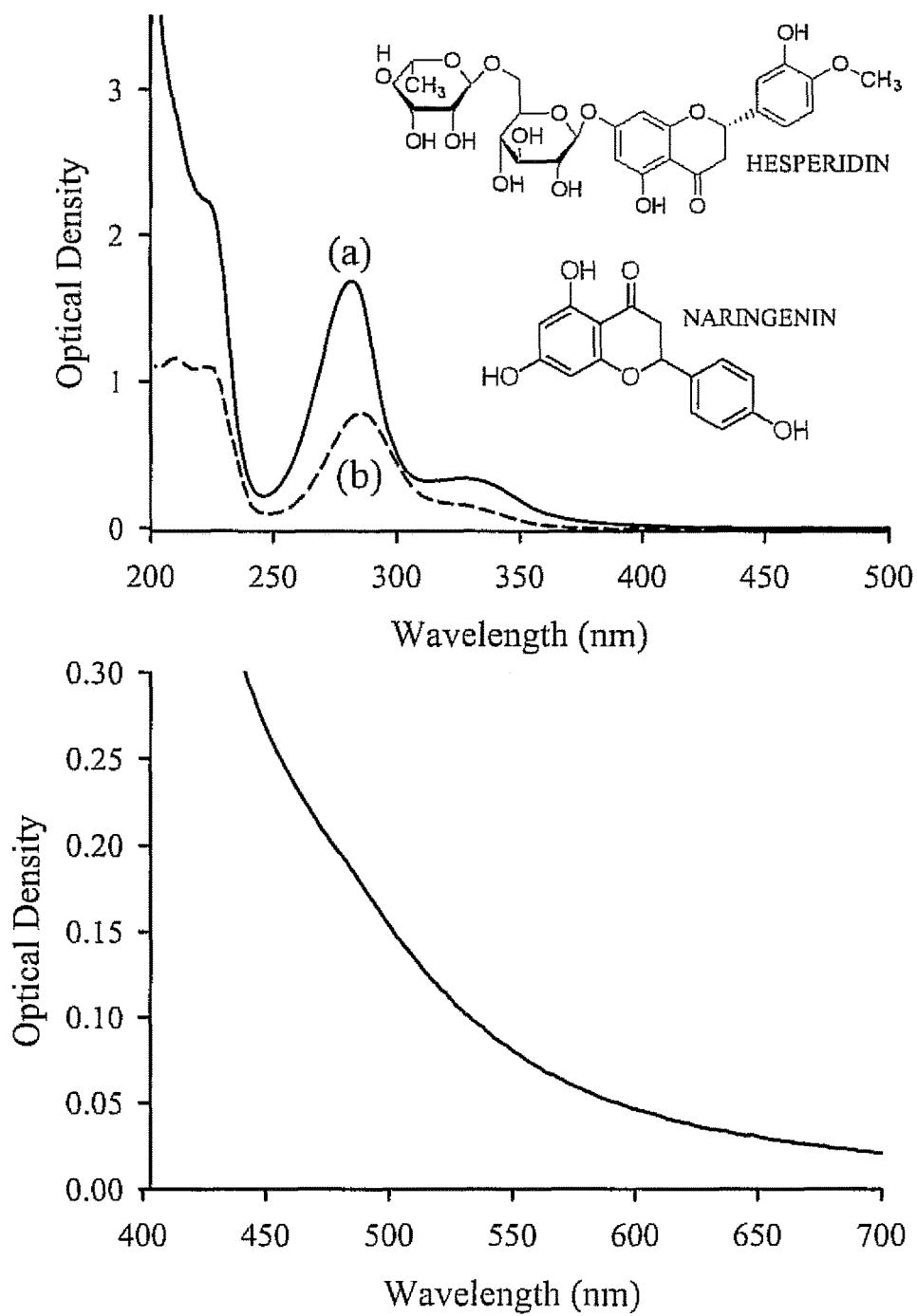
FIG. 17 shows absorption spectra of hesperidin and naringenin solutions in methanol.

The absorption properties of the flavanone examples hesperidin and naringenin are shown in FIGS. 16 and 17, and their fluorescence behavior in FIG. 18. In powder form, both compounds exhibit a very strong absorption tail up to ~900 nm, as seen in FIG. 16. For a concentrated methanol solution of naringenin, the tail extends up to about 700 nm. Long-wavelength excitation at 632 nm yields significant fluorescence intensities in the 650-700 nm region, as can be seen from FIG. 18.

Figure 19:
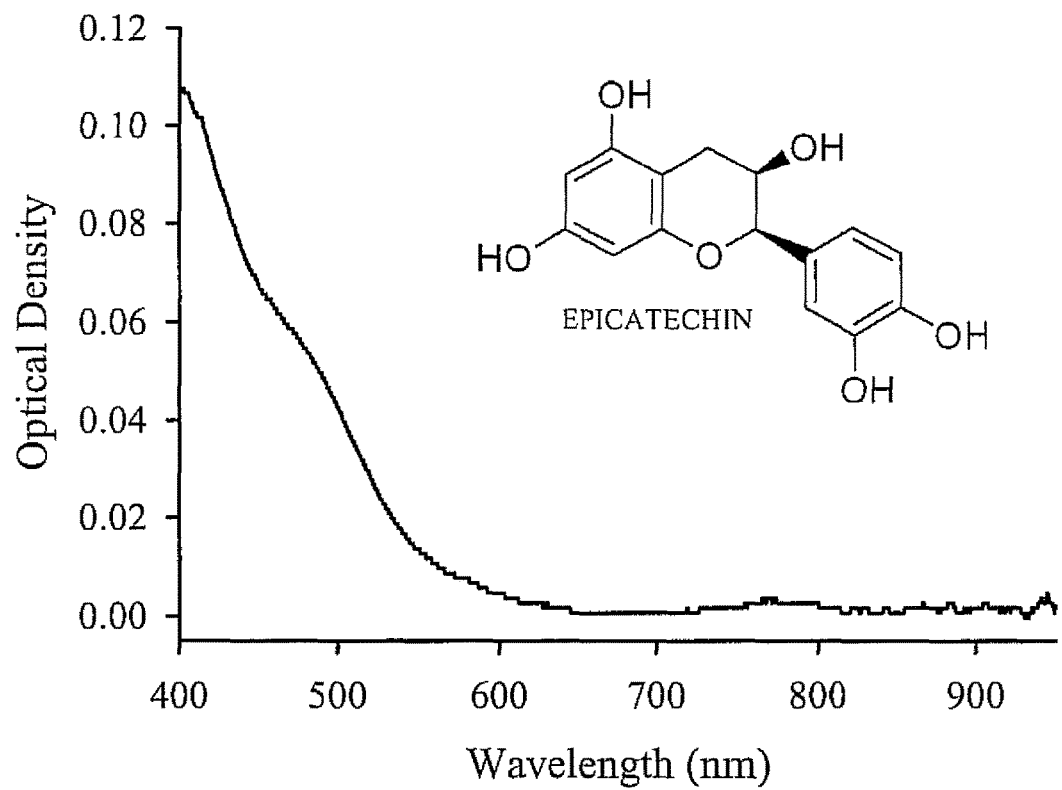
FIG. 19 shows absorption spectra of epicatechin crystal powder.
Figure 20:
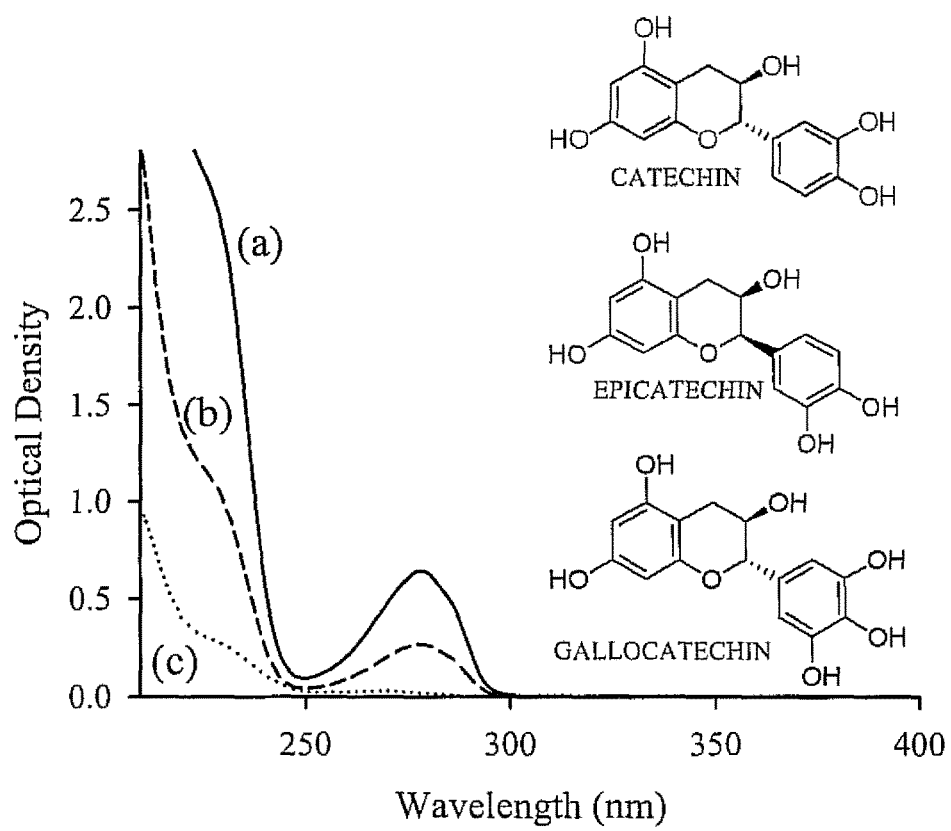
FIG. 20 shows absorption spectra for methanol solutions of catechin, epicatechin, and gallocatechin crystal powder.

The absorption behavior for catechins is shown in FIGS. 19 and 20, and their emission behavior in FIG. 21. In powder form, a strong absorption tail exists up to ~650 nm, as illustrated in FIG. 19 for epicatechin. Dissolved in methanol, the absorption tail is very weak in all cases, as seen in FIG. 20 for catechin, epicatechin and gallocatechin. All compounds, however, exhibit the familiar characteristic strong emission pattern shown in FIG. 21.

Figure 22:
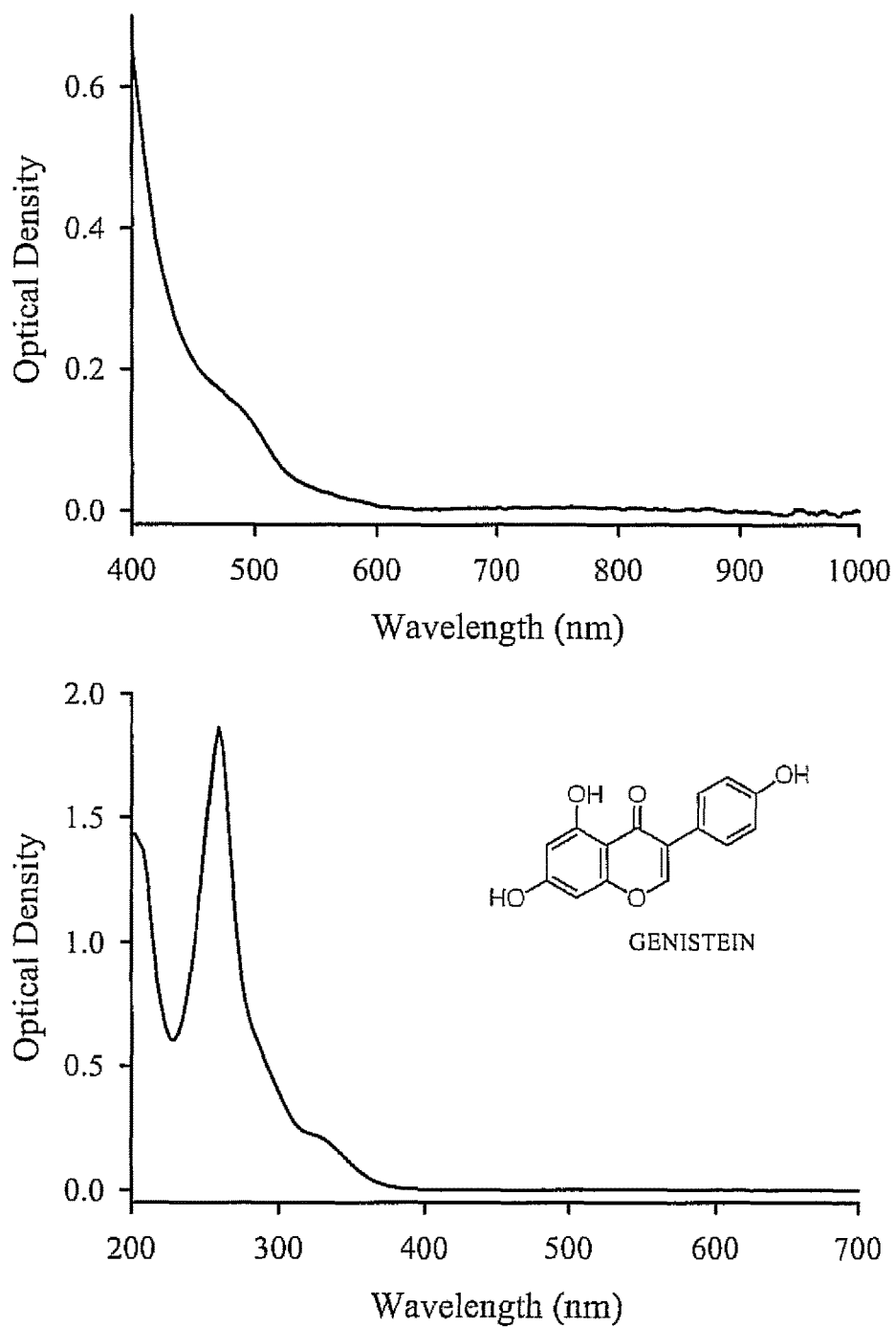
FIG. 22 shows absorption spectra of genistein crystal powder and a methanol solution of genistein.
Figure 23:
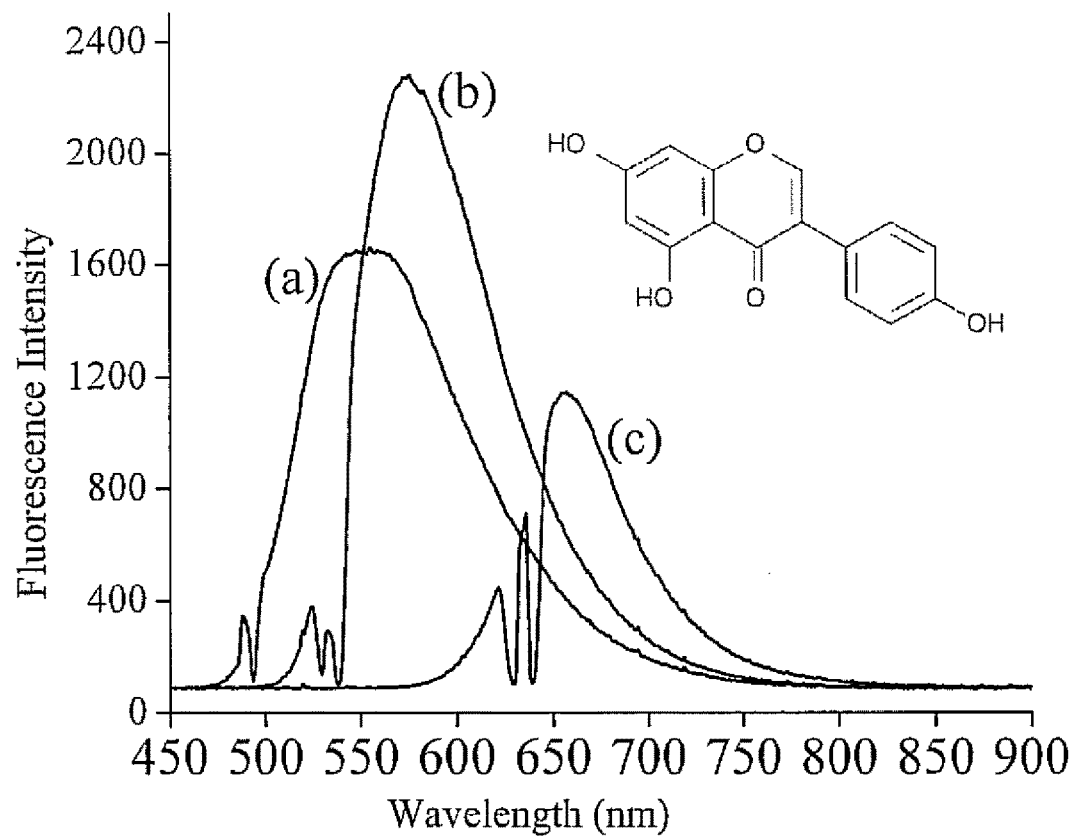
FIG. 23 shows fluorescence spectra of genistein powder at blue, green, and red excitation wavelengths.

The absorption and fluorescence properties of the isoflavone genistein are shown in FIGS. 22 and 23. In powder form, pronounced band-like absorption tails exists in the 450-900 nm range. In a methanol solution, these tails seem to disappear, as seen in FIG. 22, but fluorescence spectra reveal again significant intensities in the 650-700 nm region for this compound.

Figure 24:
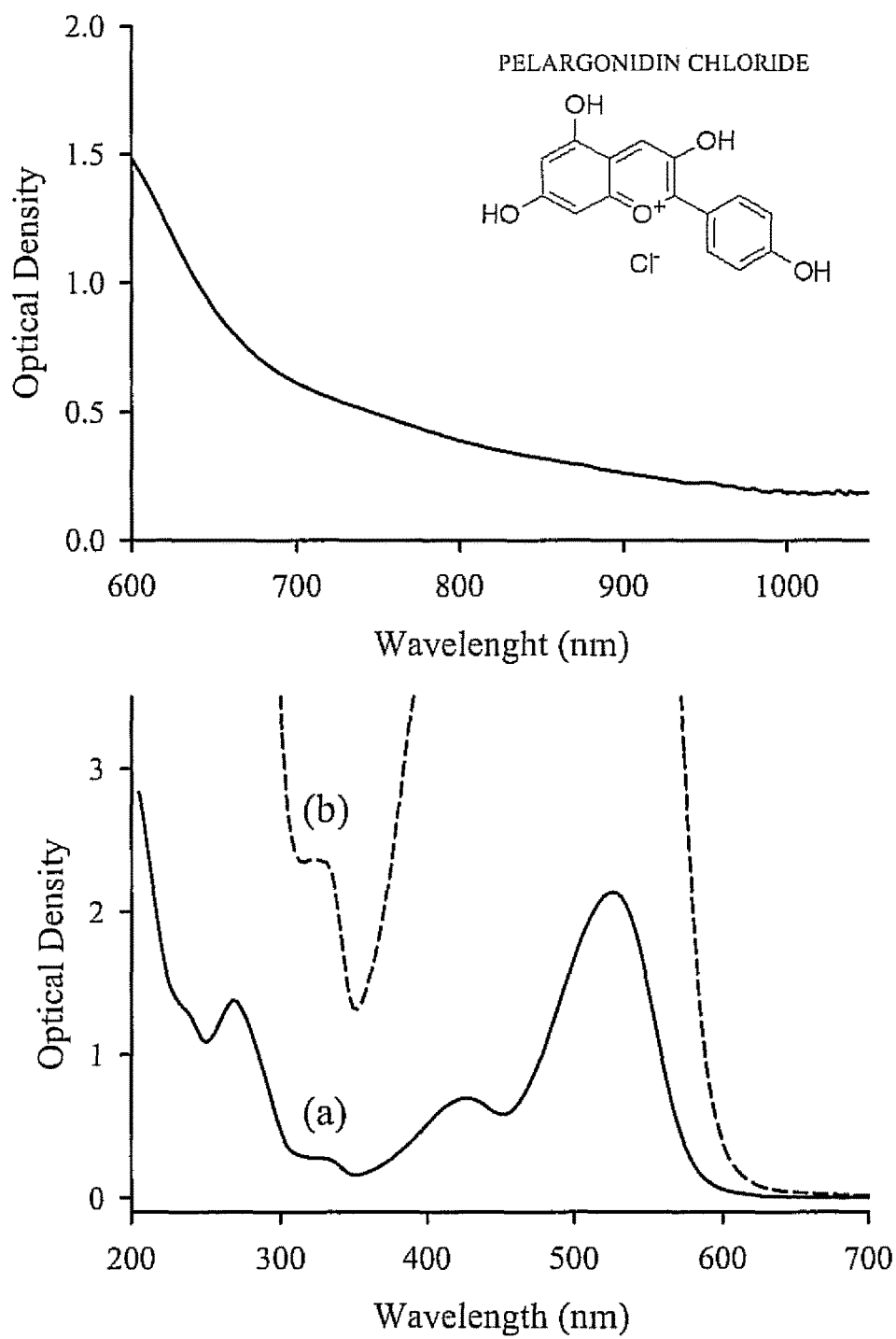
FIG. 24 shows absorption spectra of pelargonidin chloride crystal powder and two methanol solutions of the compound with low and high concentrations, respectively.
Figure 25:
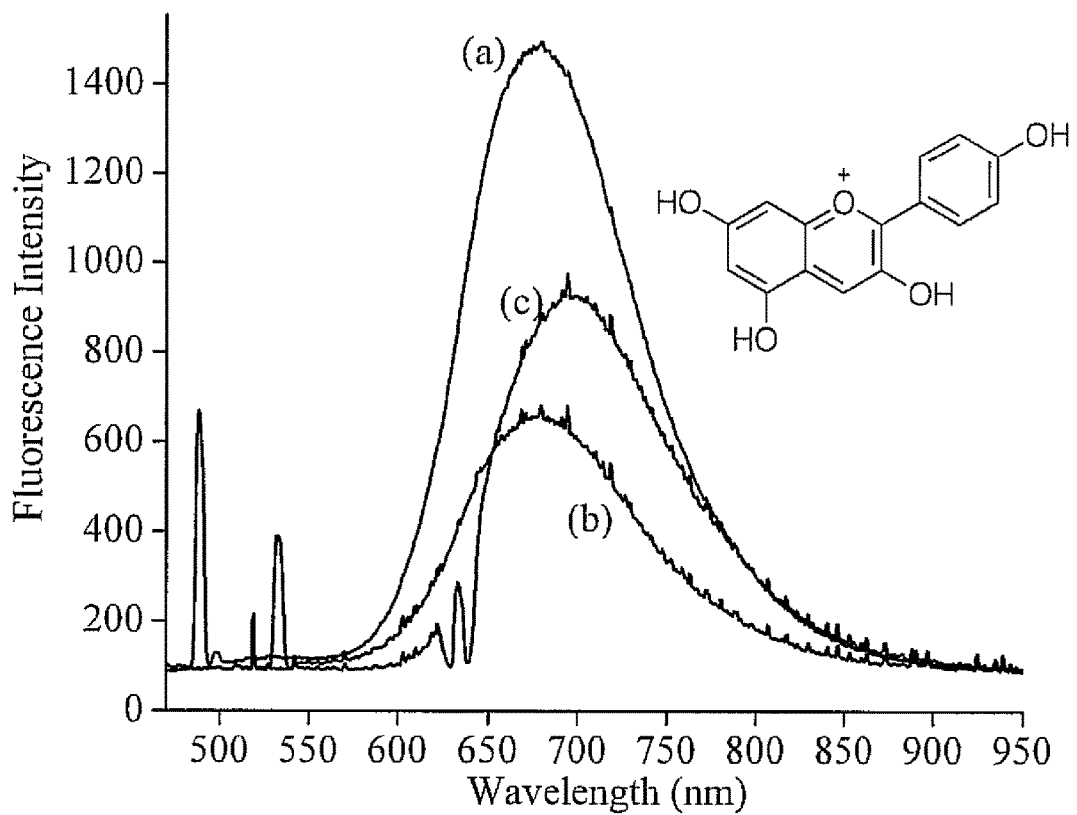
FIG. 25 shows fluorescence spectra of pelargonidin powder at blue, green, and red excitation wavelengths.

The absorption and fluorescence properties of the anthocyanidin example pelargonidin chloride, shown in FIGS. 24 and 25, differ the most from all other flavonoids. The absorption band tail is very strong, extending up to about 1000 nm in the powder sample. In a methanol solution, pronounced absorption bands appear throughout the visible wavelength region. Optical excitation yields very strong fluorescence responses at all excitation wavelengths, with the maximum of the fluorescence band occurring at ~700 nm.

Figure 26:
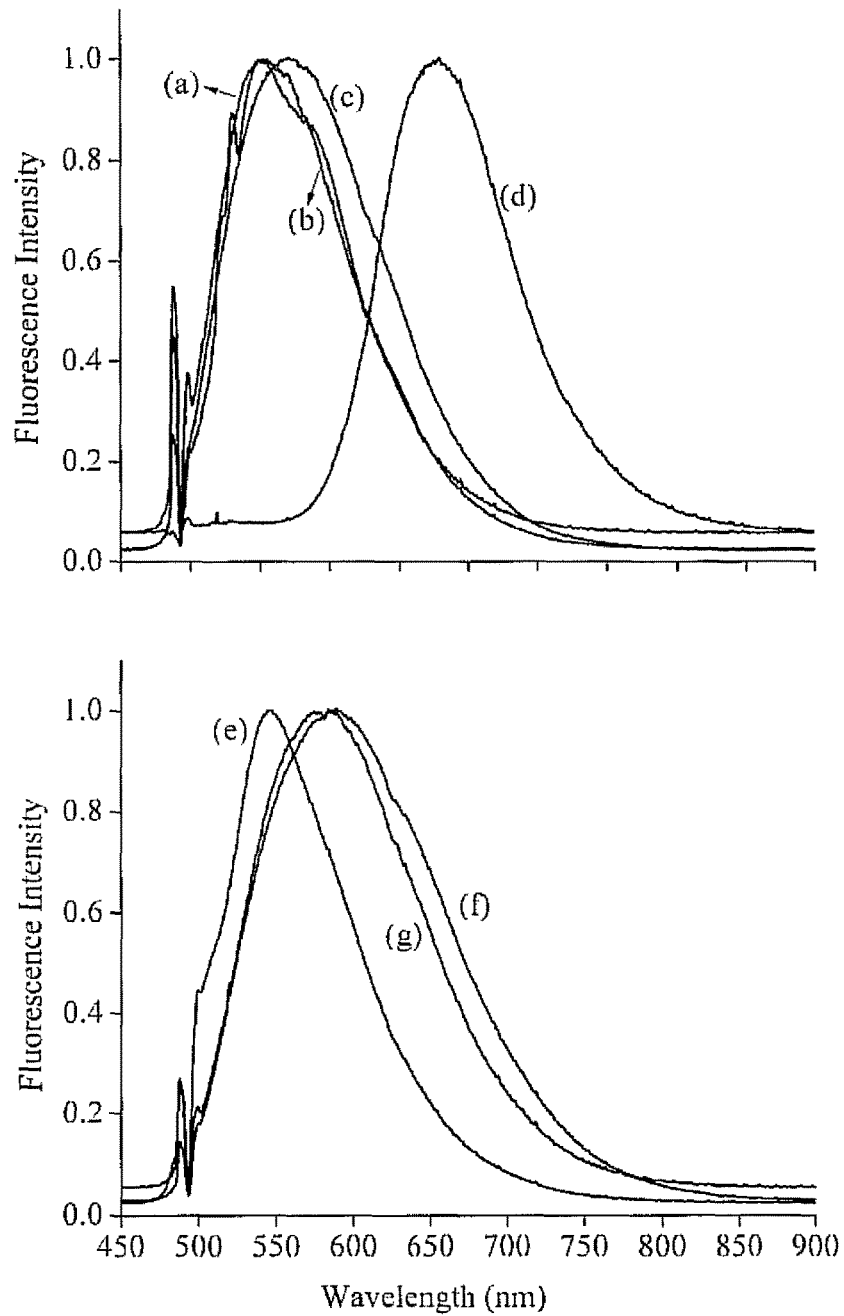
FIG. 26 shows fluorescence spectra of all investigated flavonoids, obtained with blue excitation.
Figure 27:
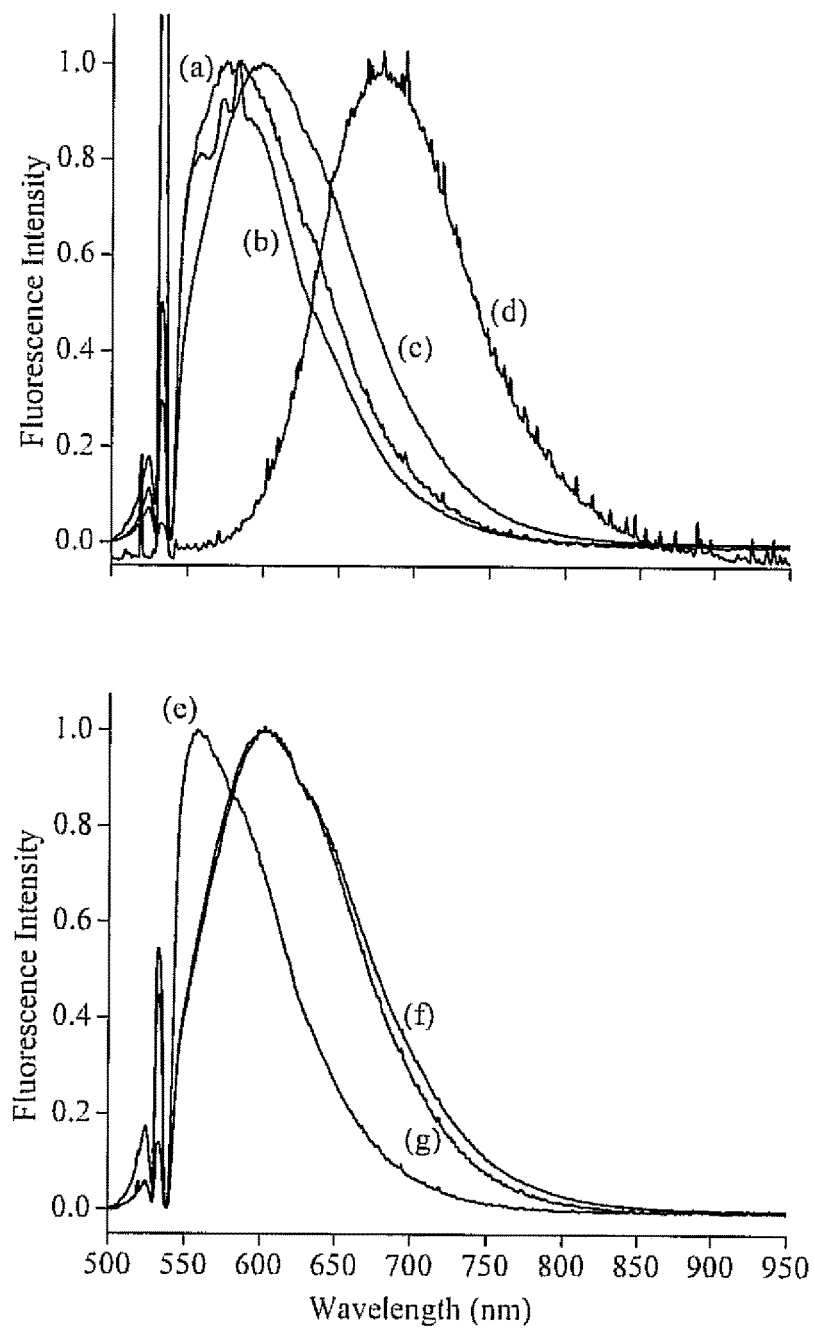
FIG. 27 shows fluorescence spectra of all investigated flavonoids, obtained with green excitation.
Figure 28:
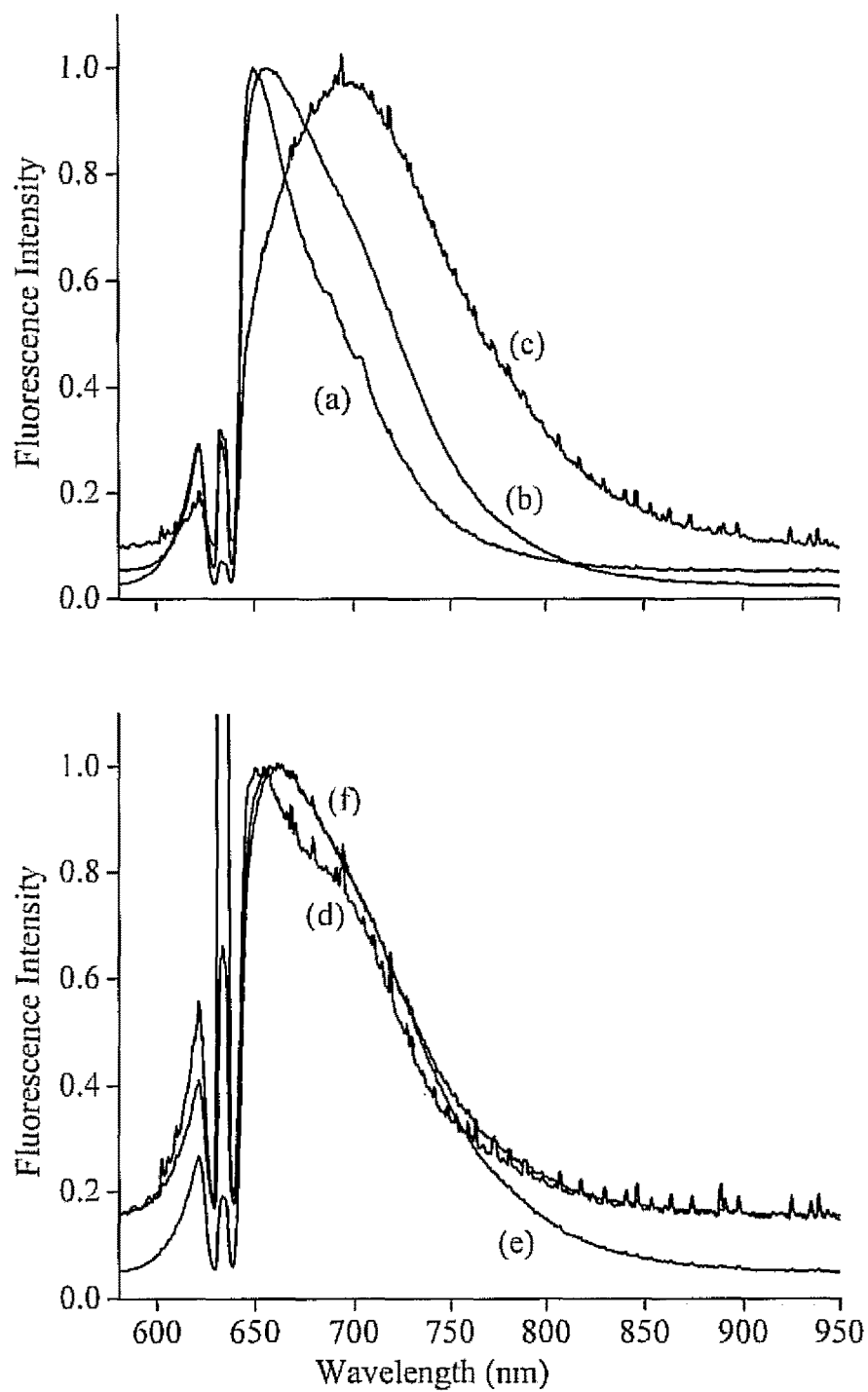
FIG. 28 shows fluorescence spectra of all investigated flavonoids, obtained with red excitation.

The similarity of the fluorescence responses for all investigated flavonoid compounds is summarized in FIGS. 26-28, where the fluorescence responses are plotted, respectively, for blue (488 nm), green (532 nm), and red (632 nm) excitations, and where the wavelength positions and spectral shapes of the bands can be compared for all investigated compounds. For each excitation wavelength, the spectral shape and position of the compounds is slightly different, with the exception of pelargodinin chloride, which is significantly shifted to longer wavelengths. Importantly, strong fluorescence signals can be obtained in all compounds even with relatively long-wavelength, red excitation.

Figure 29:
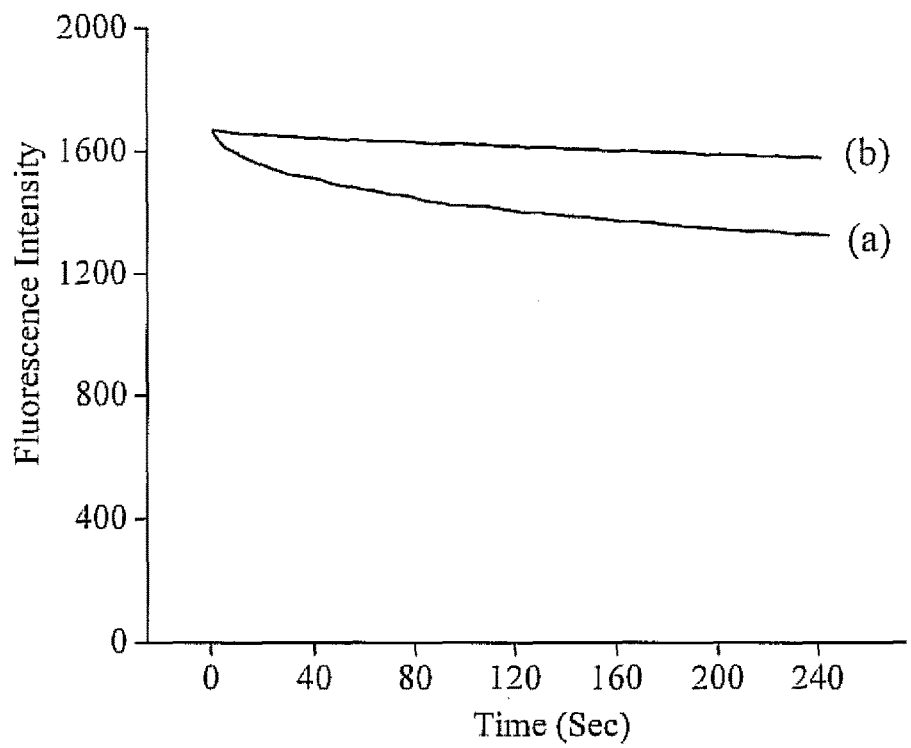
FIG. 29 shows the bleaching kinetics of quercetin crystal powder under 532 nm and 632 nm excitation.
Figure 30:
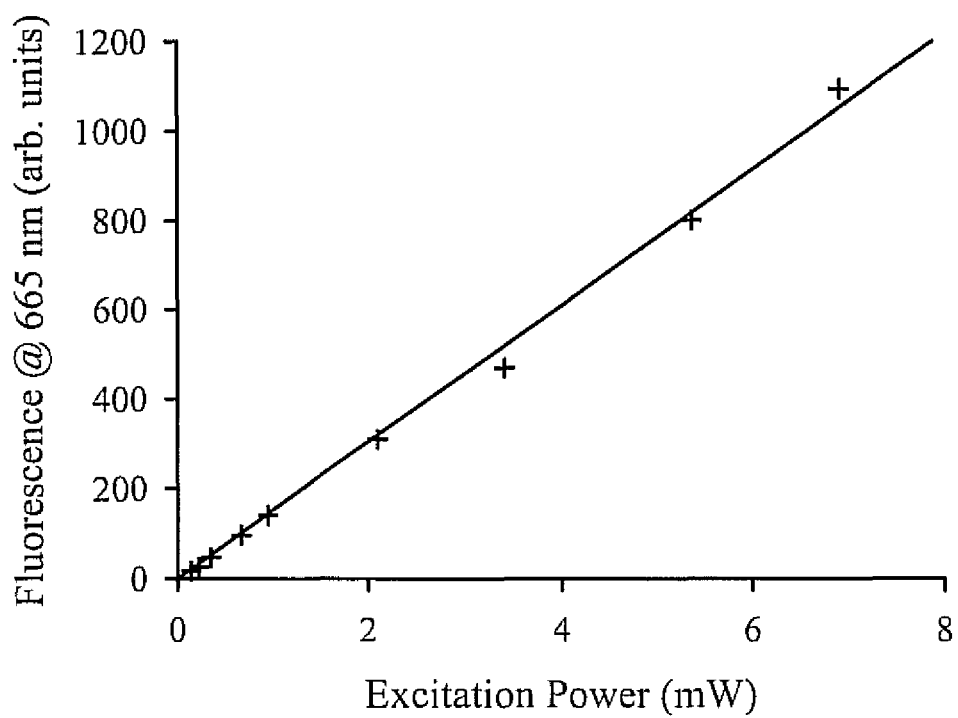
FIG. 30 shows the linearity of the fluorescence intensity of quercetin crystal powder under 632 nm excitation with increasing excitation light power.

Upon excitation the fluorescence intensity is found to decrease slightly over time, an effect illustrated in FIG. 29 for quercetin powder with 532 and 632 nm excitation. The fluorescence decay is less severe for increasing wavelengths. This effect is likely due to photoionization of the flavonoid compounds. In FIG. 30 the increase of the fluorescence intensity with excitation light power is illustrated for quercetin powder. The increase is seen to stay linear while varying the excitation light power over about two orders of magnitude.

Figure 31:
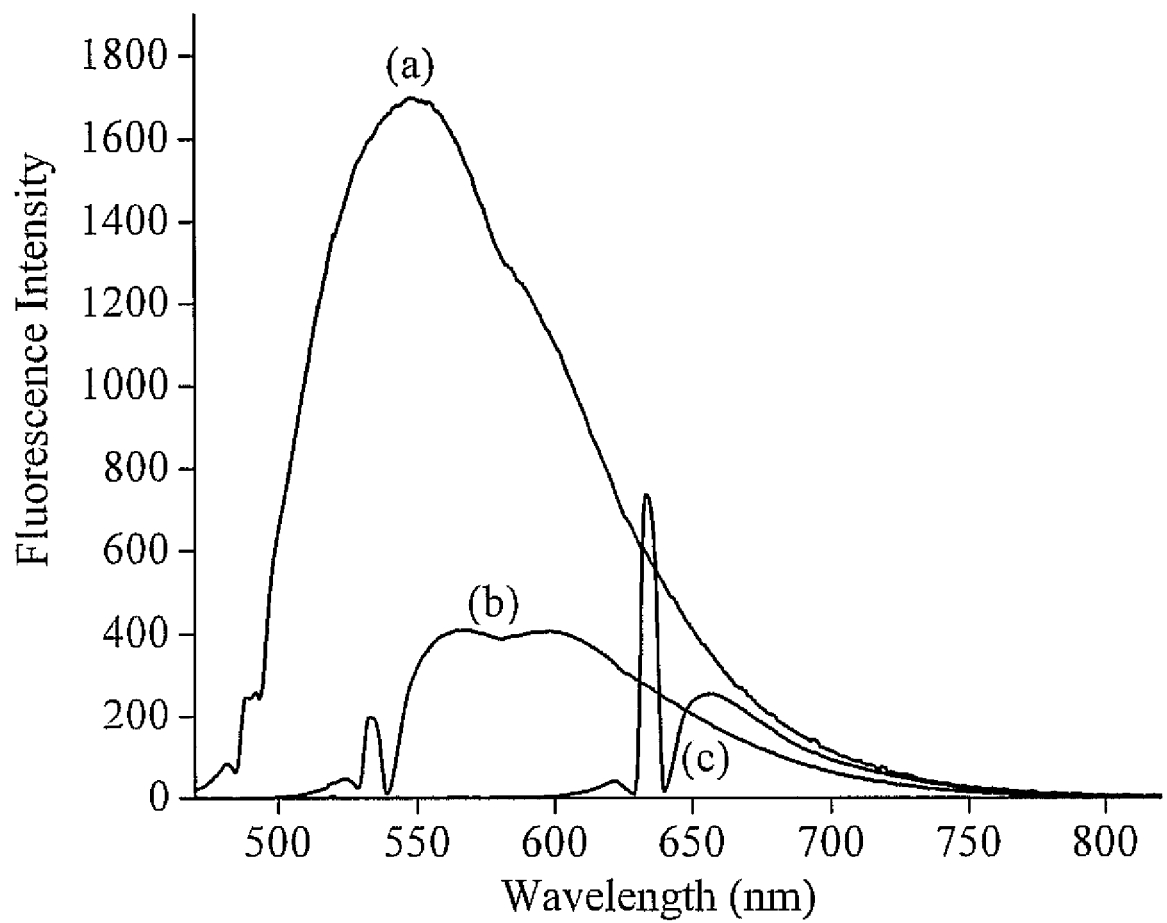
FIG. 31 shows the fluorescence spectra of living human skin for an inner palm tissue site.
Figure 32:
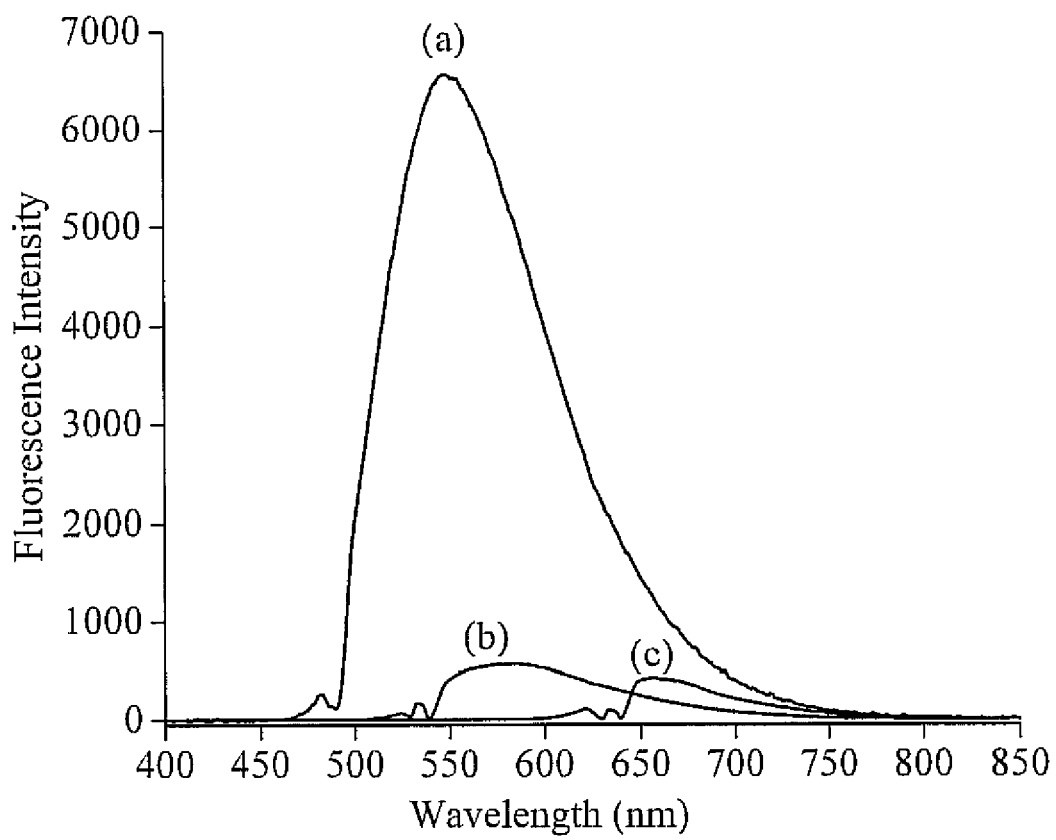
FIG. 32 shows the fluorescence spectra of an excised heel skin tissue sample.

In FIG. 31, we show the results of fluorescence measurements for a palm tissue site of living human skin, obtained under the same excitation conditions and with the same experimental setup. At all three excitation wavelengths, i.e. 488, 532, and 632 nm, broad emission bands are obtained which in positions of the spectral maxima, shapes, halfwidths, and relative strengths are very similar to the behavior of the pure flavonoid samples discussed above. A dip in the emission spectra occurs at around 570 nm, which can be attributed to the absorption of hemoglobin in the living tissue. This dip disappears when measuring a detached heel skin tissue sample, consisting essentially of a bloodless thick and relatively homogenous stratum corneum layer, as can be seen from the corresponding emission spectrum shown in FIG. 32. Compared to the pure flavonoid powder samples, the emission intensities in skin are somewhat stronger under blue excitation relative to green and red excitation wavelengths.

Figure 33:
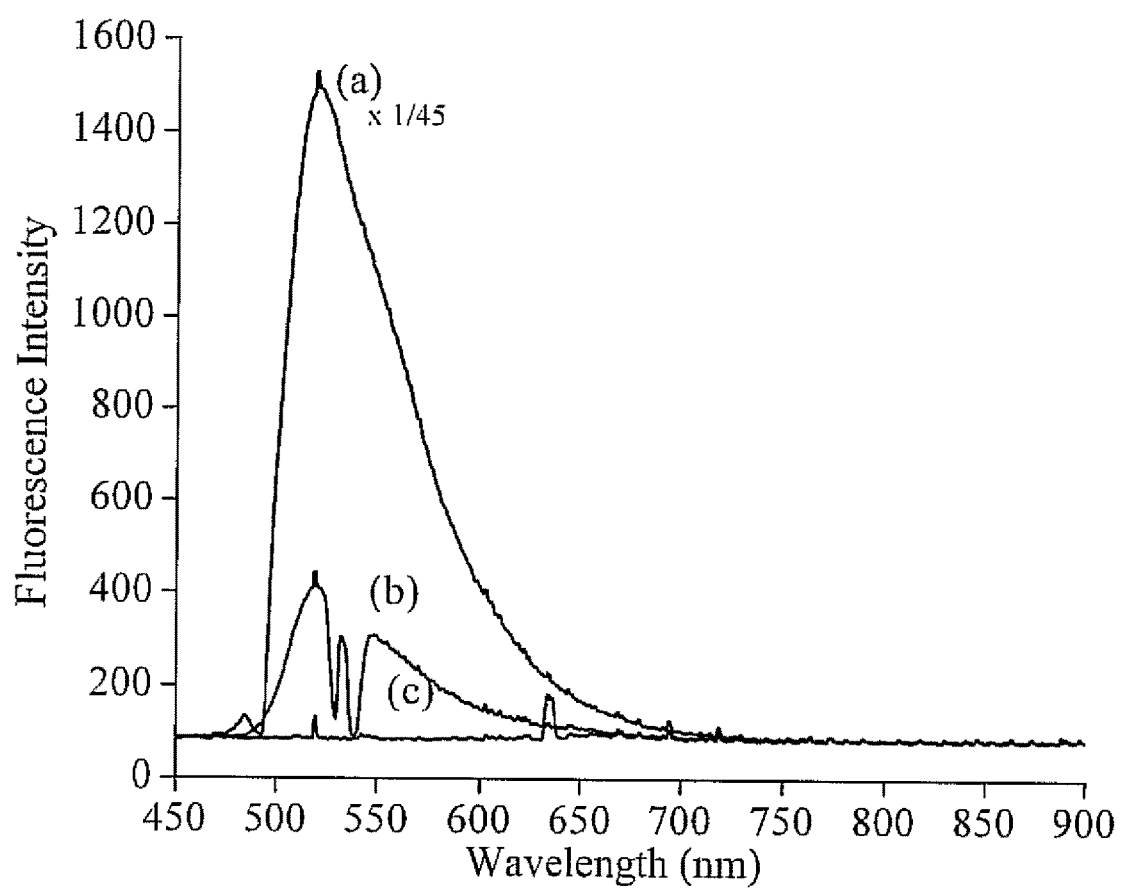
FIG. 33 shows the fluorescence spectra of collagen.

In order to investigate the potential influence of collagen tissue components onto the observed emission behavior, we excited a pure collagen sample (obtained from Sigma Aldrich) under the same excitation conditions. The fluorescence spectra obtained are shown in FIG. 33. Under blue excitation, a strong fluorescence band exists with maximum at ~540 nm. Its strength decreases rapidly with increasing excitation wavelength. Under excitation with 532 nm, the intensity drops by a factor of about 200, and under excitation with 632 nm, the obtained response consists essentially only of noise signals. This result is important since it proves that collagen does not generate any confounding fluorescence effects in the wavelength range of interest.

Figure 34:
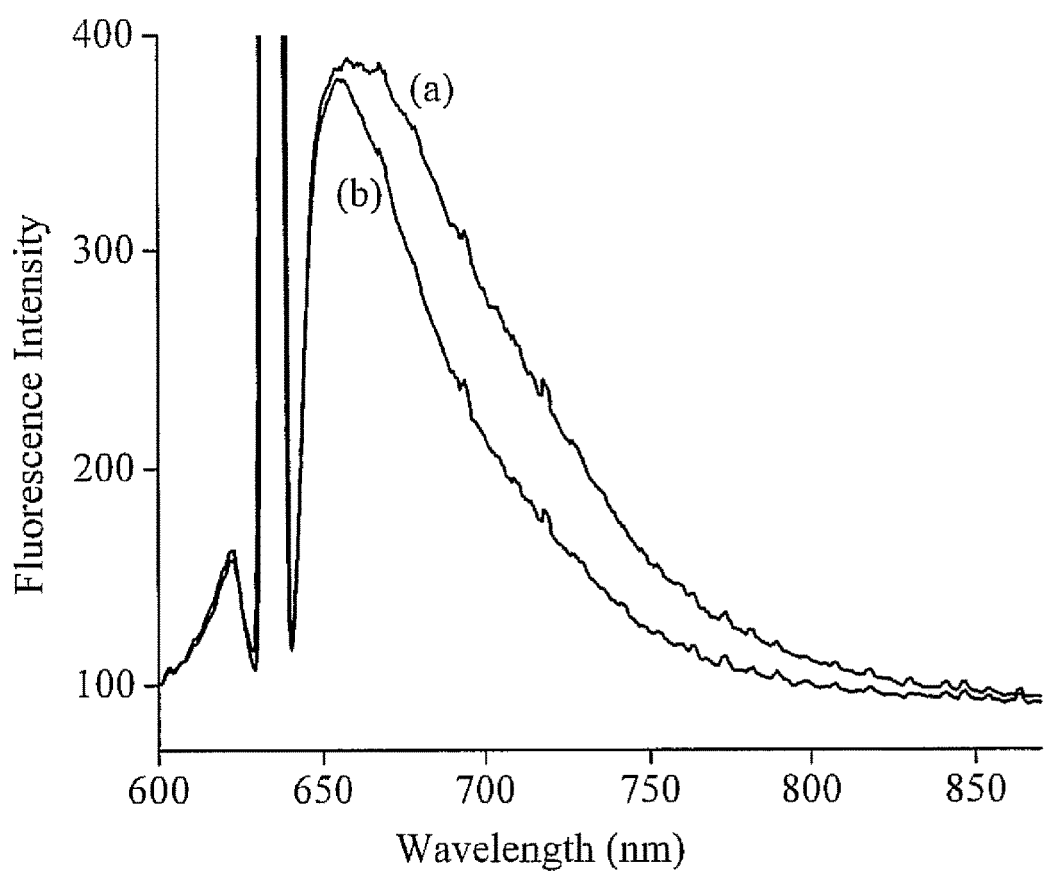
FIG. 34 shows normalized fluorescence spectra of quercetin powder and living skin.

In FIG. 34 we show, for direct comparison, the emission spectrum of living human skin, obtained with 632 nm excitation for an inner palm tissue site, along with the emission spectrum of quercetin. Clearly, the emission characteristics are very similar save for a slightly reduced bandwidth of the fluorescence in skin tissue, and we conclude therefore that it is possible to measure the presence of flavonoids in living human skin without any significant confounding effects. An exception is the influence of melanin, which acts as a passive absorber in skin tissue. This chromophore can be largely avoided, however, by using tissue sites with a thick stratum corneum layer, such the inner palm of the hand, since these sites are virtually free of melanin.

Example 2

Figure 35:
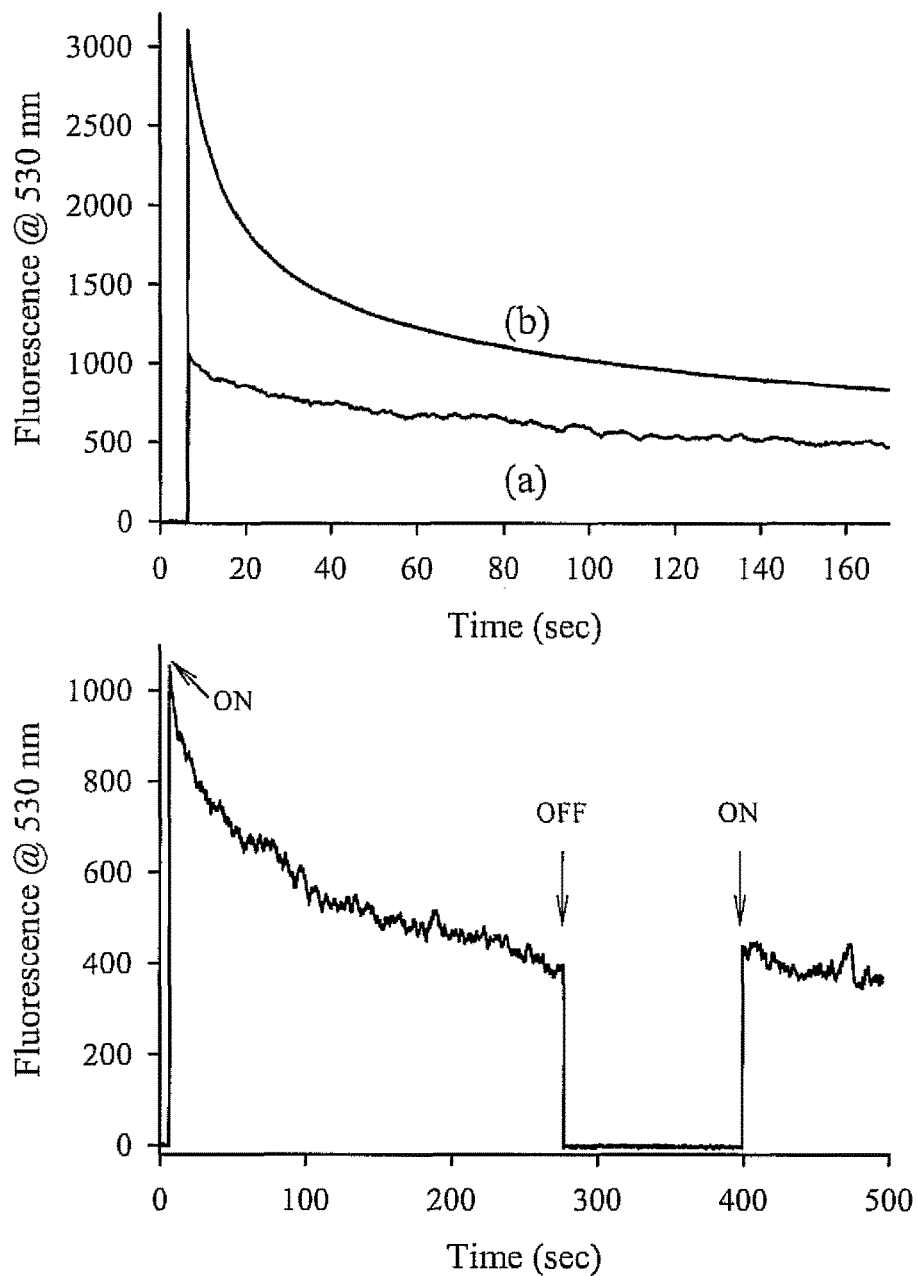
FIG. 35 shows the bleaching kinetics for living human skin in comparison with the bleaching kinetics of quercetin.
Figure 36:
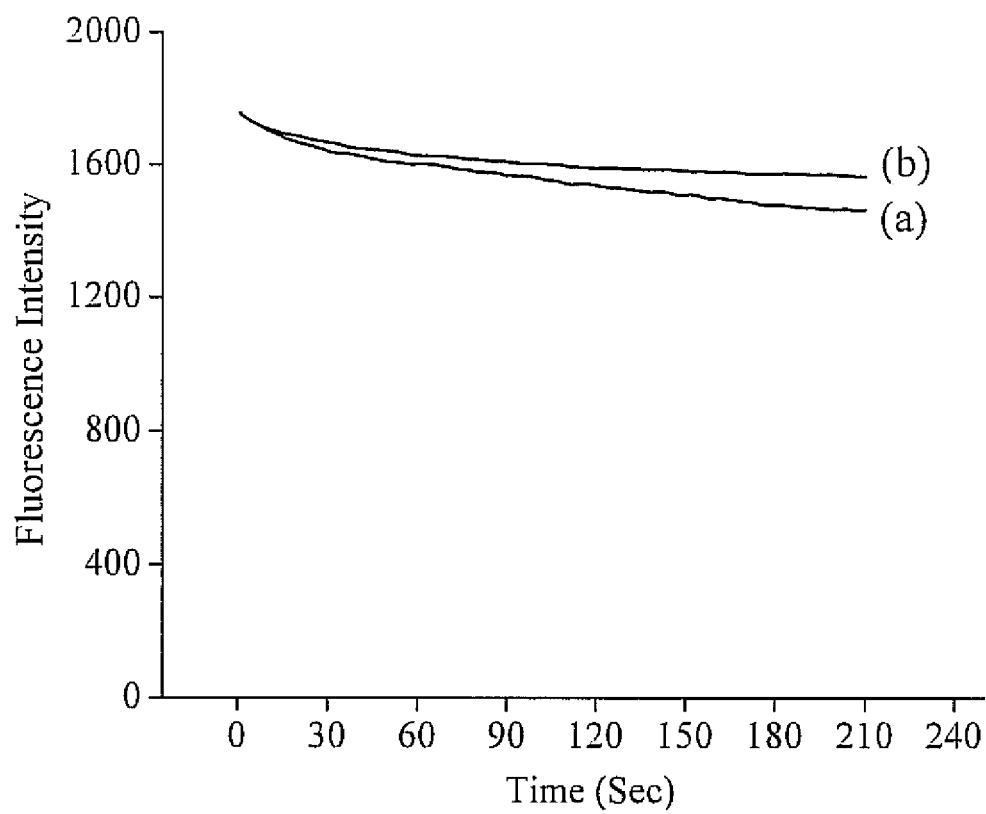
FIG. 36 shows the bleaching kinetics of living human skin.

To investigate the stability of the skin flavonoids under optical excitation conditions, we investigated potential bleaching effects of the flavonoid emission. The results are shown in FIG. 35. They are very similar to the bleaching kinetics of the pure flavonoids. Trace (a) in the top panel of FIG. 35 shows the decrease of the skin fluorescence with time under 532 nm excitation, and trace (b), for comparison, the corresponding behavior of pure quercetin powder. Very similar bleaching kinetic is observed in both cases. However, the skin fluorescence decrease is less severe than the decrease in the pure powder sample. This effect could possibly be attributed to the lower concentration of the flavonoid compounds in the skin cells as well as to their increased stability in that environment. The plot in the bottom panel of FIG. 35 shows the decrease of the skin fluorescence over time, with the excitation light turned off for 100 seconds after an initial decay period of about 300 seconds. As can be clearly seen, the fluorescence intensity does not recover to its initial level after turning the excitation light back on, thus demonstrating that the decay is irreversible, at least on the time scale of 10 minutes. The irreversible bleaching effect has to be taken into account for the optical detection of skin flavonoid content by choosing excitation in the red wavelength region, by proper reduction of excitation light power, or by decrease of the exposure time. Indeed, this can be best achieved with 632 nm excitation, as illustrated in FIG. 36, where the bleaching kinetics is compared for 532 and 632 nm excitation. Clearly, the bleaching is minimized when exciting with the longer wavelength.

Figure 37:
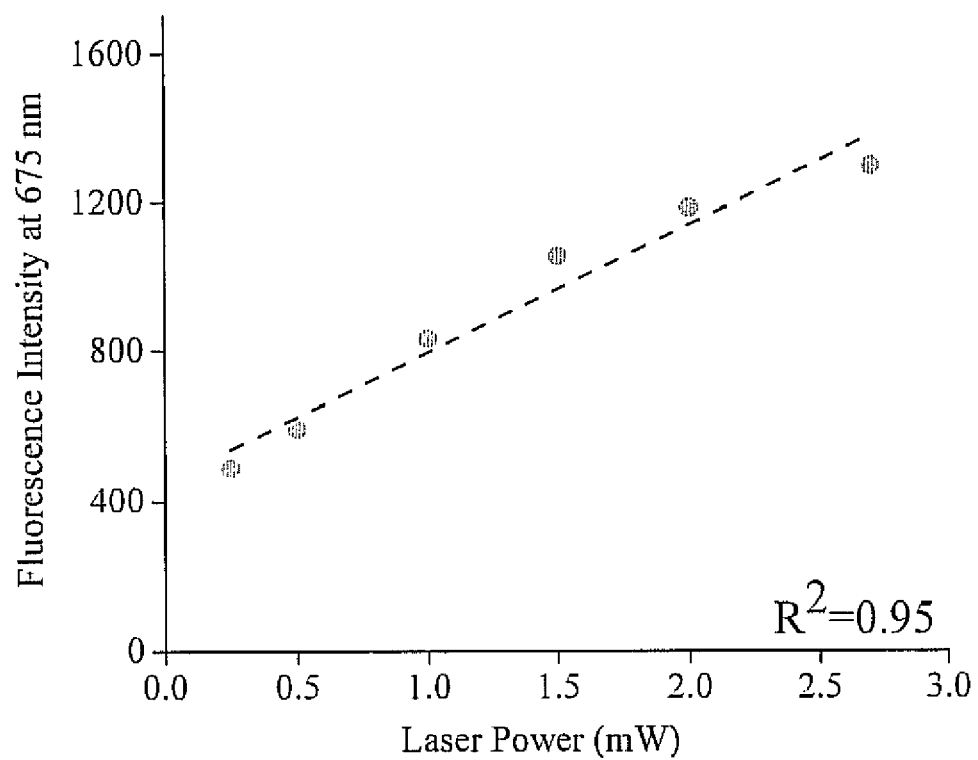
FIG. 37 shows the linearity of the fluorescence intensity of living skin with increasing excitation light power.

In FIG. 37 we plot the variation of skin fluorescence with increasing 632 nm excitation light power. We observe a linear increase of the skin fluorescence intensity with increasing excitation light power from low levels of about 0.3 mW up to 3 mW. Thus, under these conditions, the skin fluorescence response is linear, and it can be used as a measure of flavonoid concentration in the illuminated tissue volume. We established that useful fluorescence measurements of living human skin could be accomplished using a laser power of less that about 2 mW, and an exposure time of 5 seconds. Taking into account an approximately 1.5 mm diameter laser light spot size on the skin, this results in an intensity of about 0.11 $W/cm^2$ at the skin surface, which is considered safe by ANSI Z136.1-2000 standards [11]. In fact, for the used laser intensity on the skin, the exposure time required for a measurement is about a factor of 1000 below the exposure limit set by this safety standard.

Figure 38:
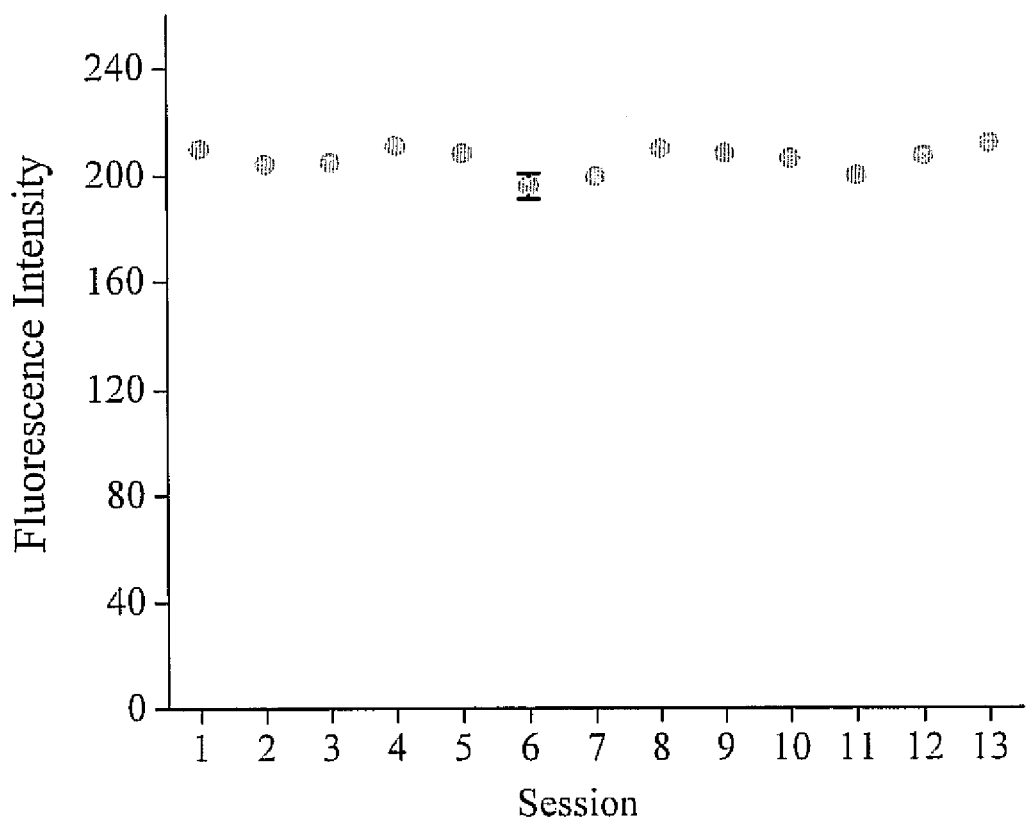
FIG. 38 shows the repeatability of the skin fluorescence for successive measurements.

The repeatability of the skin flavonoid measurements under these conditions is shown in FIG. 38, where the skin flavonoid fluorescence intensity in the maximum of the band at ~660 nm is plotted for a palm tissue site of a volunteer subject for 13 repeated measurements. Repeatability is better than about 10%.

Example 3

Figure 39:
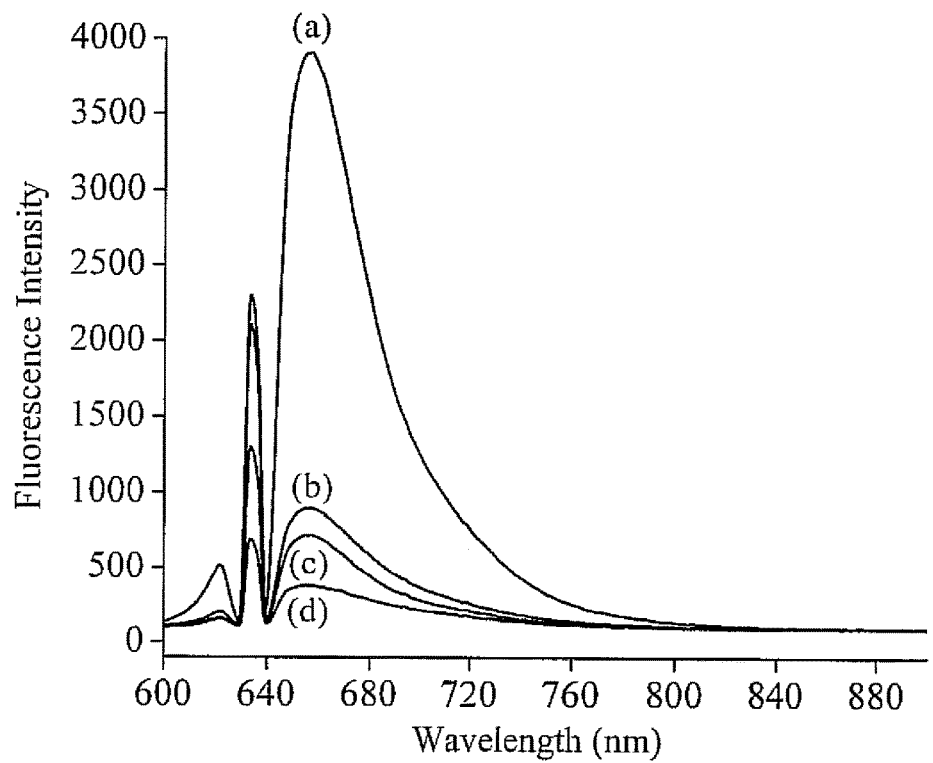
FIG. 39 shows skin fluorescence spectra for various tissue sites.

To test the optimum tissue site for optical detection of skin flavonoids, we investigated several skin tissue sites, using identical excitation and detection conditions. The results are shown in FIG. 39 for the tissue sites tip of an index finger, curve (a), tip of a thumb, curve (b), inner volar forearm, curve (c), and inner palm, curve (d). By far the highest flavonoid response is seen to originate from the index finger tissue site. This is likely due to the thin stratum corneum layer in this tissue site, which reduces scattering of excitation and emission wavelengths upon tissue propagation, and therefore allows for increased optical penetration into the tissue volume. However, sufficiently strong fluorescence signals are obtainable even for the palm tissue site, which has the advantage of the thickest stratum corneum among the tested tissue sites. Due to the strong scattering of the stratum corneum this has the advantage of limiting the light penetration to less dermal layers, and thereby reducing the effects of potentially confounding deeper, blood containing skin layers.

Example 4

Figure 40:
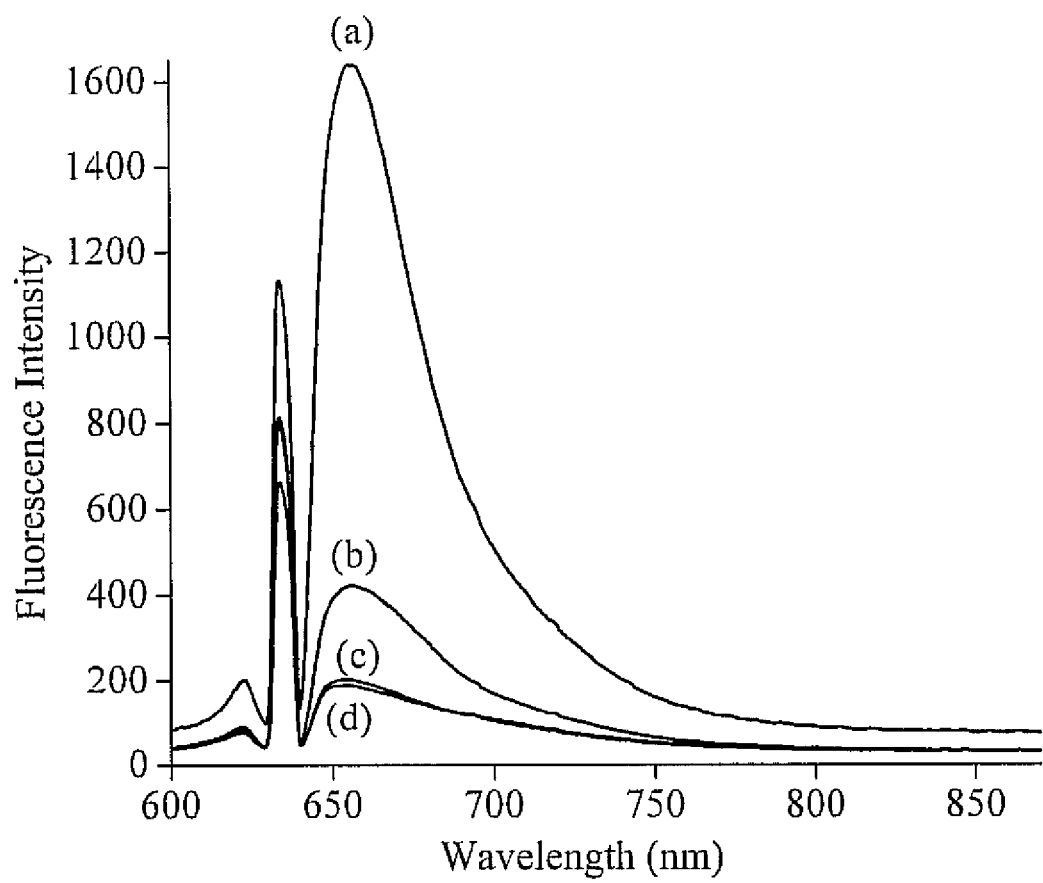
FIG. 40 shows skin fluorescence spectra for four different volunteer subjects.

Using as a skin tissue site the inner palm, and 632 nm excitation, we measured the skin flavonoid emission response in several volunteer subjects. The results are shown in FIG. 40. They demonstrate the same spectral shape in all subjects, but a large inter-subject variability in emission strength, and hence flavonoid content. The optical flavonoid detection method is therefore useful to assess skin flavonoid levels non-invasively, to compare flavonoid status between subjects, and to track the status over time.

Example 5

Figure 41:
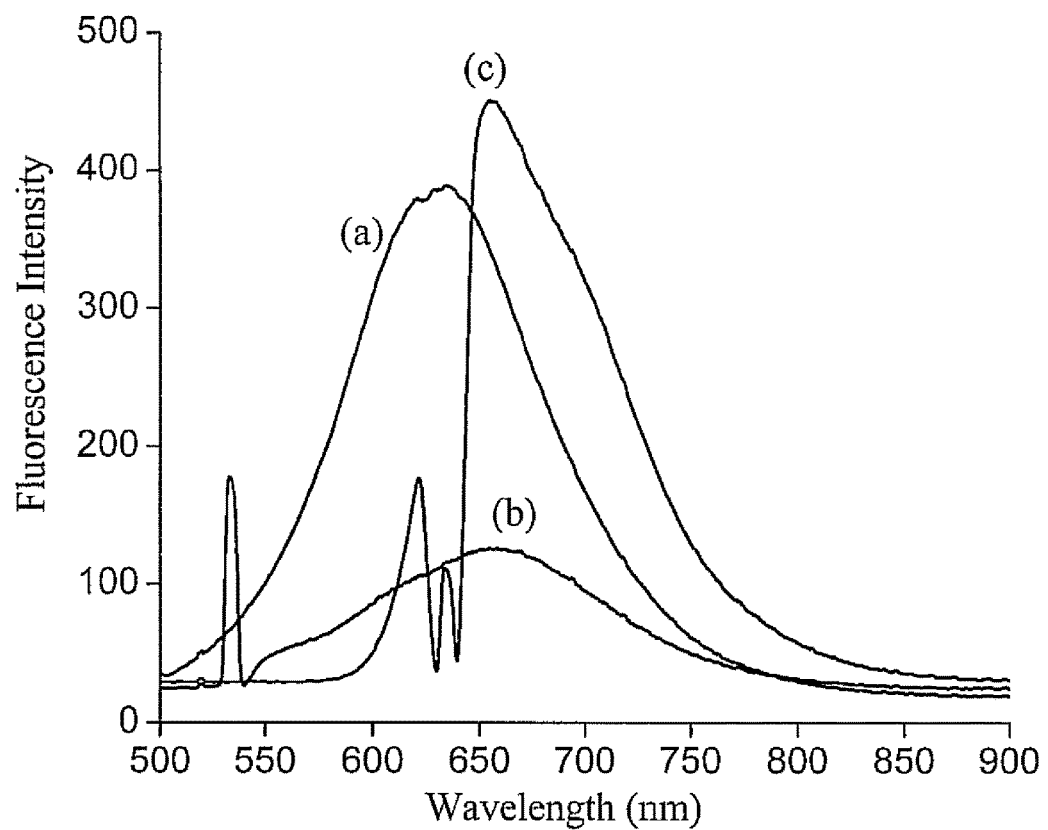
FIG. 41 shows fluorescence spectra of an onion layer, obtained with blue, green, and red excitation.
Figure 42:
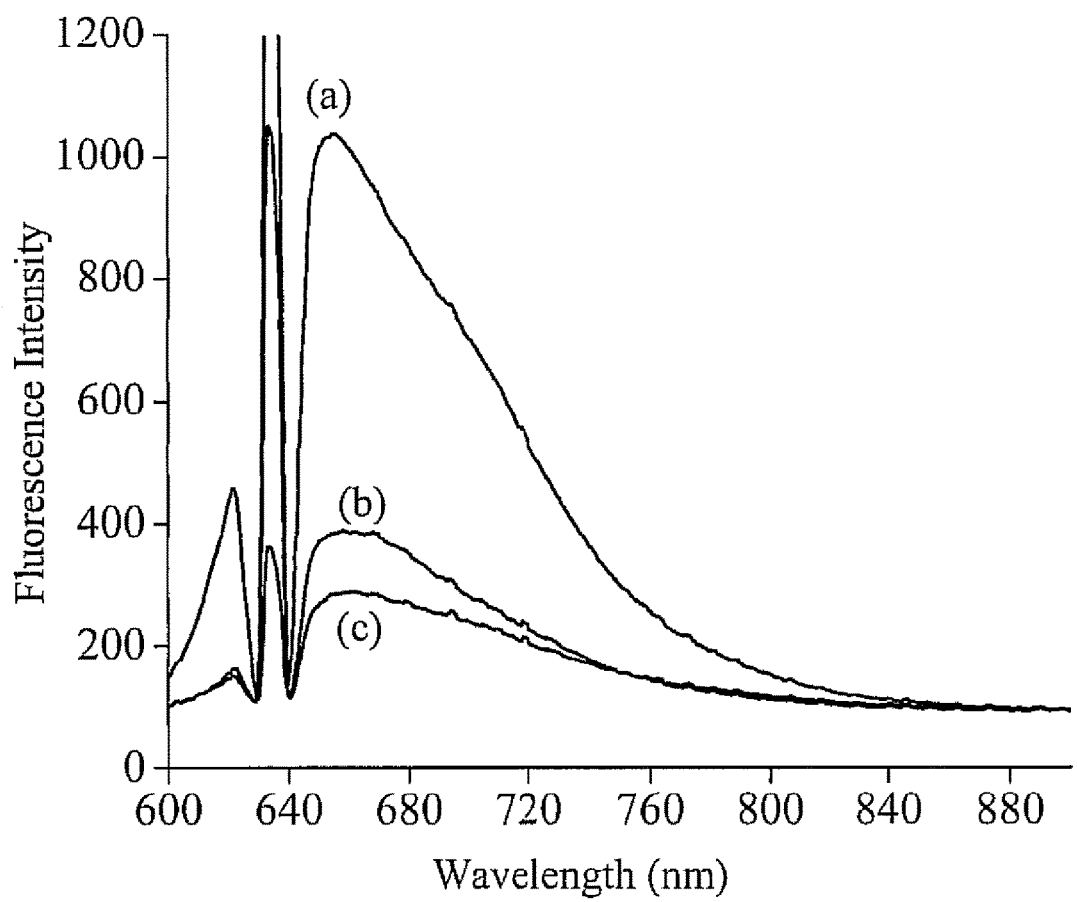
FIG. 42 shows a comparison of the fluorescence spectrum of an onion layer with fluorescence spectra of quercetin and kaempferol, all obtained under red excitation.
Figure 43:
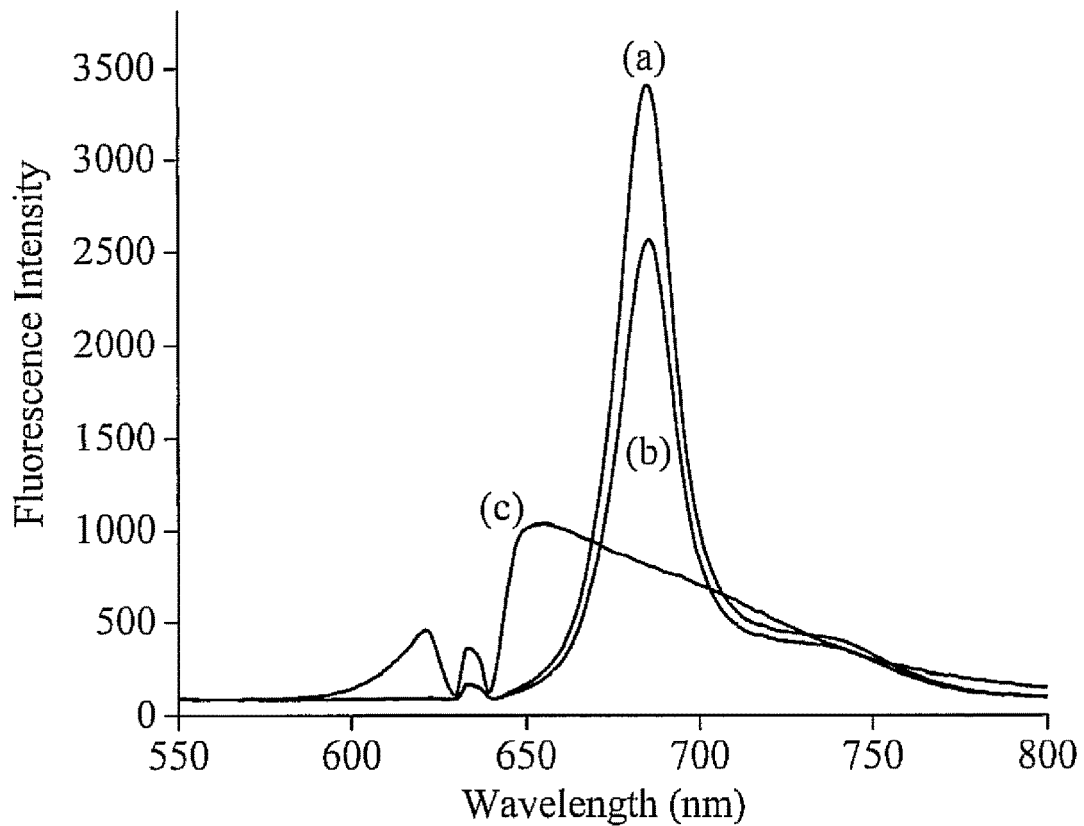
FIG. 43 shows fluorescence spectra of a green grape, a red grape, and an onion layer.

Certain flavonoids are selectively concentrated in certain fruits and vegetables, like quercetin in the outer ring layer of onions. After removal of the outer skin, onion samples are optically clear in the visible wavelength range, and therefore well suited for flavonoid excitation and fluorescence measurements. Using the setup of FIG. 3, we measured the emission of a sample under 488, 532, and 632 nm excitation. The result is shown in FIG. 41. The emission behavior is very similar again to that of the pure flavonoid samples of FIG. 6, featuring almost identical maxima of the emission bands, reduced halfwidths and spectral shifts with increasing excitation wavelengths. In FIG. 42, the emission behavior of the onion sample obtained under 632 nm is compared directly with the emission spectra of pure quercetin and kaempferol. Clearly, the shape of the emission spectra is very similar, suggesting that the emission spectra of the onion sample is indeed due to flavonoids, and that the fluorescence spectroscopy method described in this patent application, is suitable also for the noninvasive flavonoids measurement of vegetables having sufficient optical clarity in the wavelength range of interest. Even in samples with potentially confounding concentrations from other pigments, the optical detection method may still be viable. An example is FIG. 43, in which the fluorescence spectra obtained with 632 nm excitation are shown for red and green grape samples containing other pigments than flavonoids. The fluorescence of these pigments appears in a narrow band centered at ~680 nm, and is clearly distinguishable from the fluorescence of flavonoids, such as those in the onion sample, which again is shown for comparison, and in which the fluorescence is peaking near 660 nm.

Example 6

Figure 44:
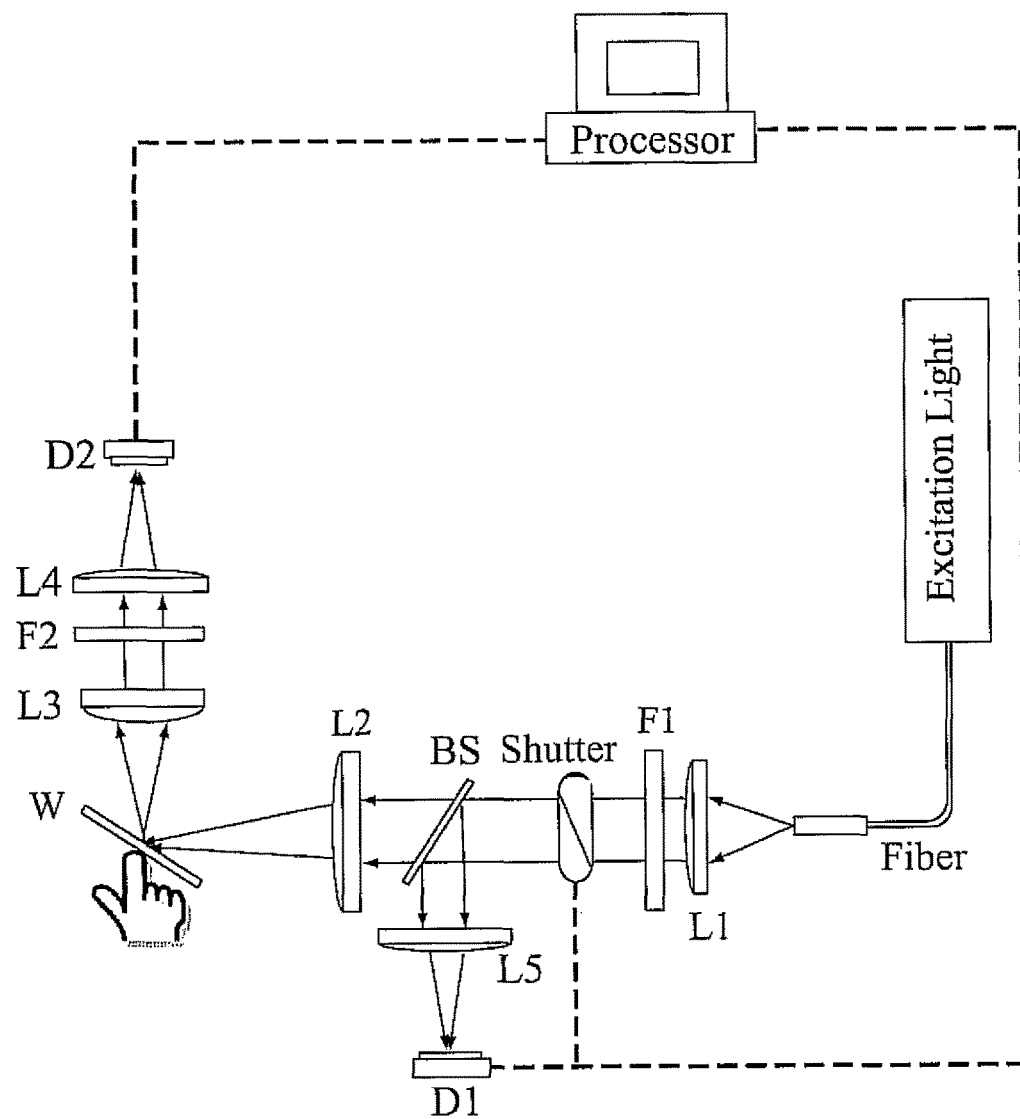
FIG. 44 shows a filter-based experimental setup for flavonoid fluorescence measurements.

For the optical detection of flavonoids in living human tissue it may be possible to facilitate the required instrumentation by eliminating the spectrograph and to use instead a filter based optical setup—at least in the case of melanin-free skin tissue sites and at red excitation wavelengths avoiding confounding chromophores. Basically, such an instrument which is sketched in FIG. 44, and which would be economically very attractive, would consist of a simple excitation beam path that illuminates the tissue site of interest with a filtered light source. Furthermore, it would contain a detection beam path that collects the fluorescence from the skin tissue via collimator, filters the emission with a suitable long pass filter, and quantifies the emission intensity via photodiode/computer combination.

REFERENCES

1. Formica J V, Regelson W, Review of the biology of quercetin and related bioflavonoids, Food Chem. Toxicol. 1995; 33:1061-80.
2. Flavonoids: Chemistry, Biochemistry, and Applications, O. M. Andersen and K. R. Markham, Eds., CRC Press, Taylor & Francis Group, LLC, 2006.
3. Hanneken A, Lin F-F, Johnson J, Maher P 2006, Investigative Ophthalmology & Visual Science 47, 3164-77.
4. Rice-Evans C A, Miller N J, Paganga G, *Free Radic. Biol. Med.* 1996; 20:933.
5. Bohm B A, *Introduction to Flavonoids. Chemistry and Biochemistry of Organic Natural Products.* Harwood Academic Publisher: Amsterdam, 1998:200.
6. Jurasekova Z, Garcia-Ramos J V, Domingo C, Sanchez-Cortes S, *Surface-enhanced Raman scattering of flavonoids*, J. Raman Spectrosc. 2006; 37: 1239-1241.
7. Cornard J P, Merlin J C, Boudet A C, Vrielynck L, http://www3.interscience.wiley.com/journal/56500/issue
8. Cornard J P, Dangleterre, Lapouge C 2005, J. Phys. Chem. A; 109:10044-10051.
9. Gellermann W et al., U.S. Pat. No. 6,205,354 B1.
10. Lotito S B, Frei B 2006; Free Radic. Biol. Med. 41 (12): 1727-46.
11. American National Standards Institute, *American National Standard for Safe Use of Lasers*, ANSI Z136.1-2000, Laser Institute of America, Orlando, Fla. (2000).

We claim:
1. A noninvasive method of measuring flavonoid levels in biological tissue, comprising the steps of:
  illuminating a localized region of tissue with light having wavelength from about 500 to 700 nm to overlap the long-wavelength absorption band tail of a flavonoid compound;
  detecting the fluorescence emitted by the flavonoid compound resulting from the illumination; and
  determining the concentration level of the flavonoid compound based upon the detected fluorescence.

2. The method of claim 1, including the step of using the concentration level to assess the antioxidant status of the tissue.

3. The method of claim 1, including the step of comparing the concentration level to levels of normal biological tissue to assess the risk or presence of a malignancy or other disease.

4. The method of claim 1, wherein the step of detecting the fluorescence emitted by the flavonoid compound includes the use of fluorescence spectroscopy.

5. The method of claim 1, wherein the step of detecting the fluorescence emitted by the flavonoid compound includes the use of an optical detector.

6. The method of claim 5, wherein the light is in the red region of the spectrum.

7. The method of claim 5, wherein the localized region of tissue is substantially melanin-free.

8. The method of claim 1, wherein the tissue is human skin.

9. The method of claim 8, wherein the skin is on a fingertip or other portion of a hand.

10. The method of claim 1, wherein the illumination is outside the absorption range of potentially confounding skin chromophores.

11. The method of claim 1, wherein the illumination excites the tissue flavonoids in their long-wavelength absorption tail outside the absorption range of other skin chromophores.

12. The method of claim 10, wherein the chromophores include carotenoids, blood, elastin, and collagen.

13. The method of claim 11, wherein the chromophores include carotenoids, blood, elastin, and collagen.

14. A system for measuring flavonoid levels in biological tissue noninvasively, comprising:
a source of light for illuminating a localized region of tissue with light that overlaps the absorption bands of a flavonoid compound;
a device for detecting the fluorescence emitted by the flavonoid compound resulting from the illumination; and
a processor for determining the concentration level of the flavonoid compound based upon the detected fluorescence.

15. The system of claim 14, wherein the processor is operative to assess the antioxidant status of the tissue based upon the concentration level.

16. The system of claim 14, further including a memory for storing flavonoid concentration levels associated with normal biological tissue; and
wherein the processor is operative to compare the determined concentration level to the stored levels to assess the risk or presence of a malignancy or other disease.

17. The system of claim 14, wherein the device for detecting the fluorescence emitted by the flavonoid compound includes a fluorescence spectrograph in electrical communication with the processor.

18. The system of claim 14, wherein the device for detecting the fluorescence emitted by the flavonoid compound includes an optical detector in electrical communication with the processor.

19. The system of claim 18, wherein the source of light is in the red region of the spectrum.

20. The system of claim 18, wherein the localized region of tissue is substantially melanin-free.

21. The system of claim 14, wherein the tissue is human skin.

22. The system of claim 21, wherein the skin is on a fingertip or other portion of a hand.

23. The system of claim 14, wherein the source of light is outside the absorption range of potentially confounding skin chromophores.

24. The system of claim 14, wherein the source of light excites the tissue flavonoids in their long-wavelength absorption tail outside the absorption range of other skin chromophores.

25. The system of claim 23, wherein the chromophores include carotenoids, blood, elastin, and collagen.

26. The system of claim 24, wherein the chromophores include carotenoids, blood, elastin, and collagen.

* * * * *

UNITED STATES PATENT AND TRADEMARK OFFICE
CERTIFICATE OF CORRECTION

PATENT NO. : 9,814,417 B2
APPLICATION NO. : 12/352702
DATED : November 14, 2017
INVENTOR(S) : Mohsen Sharifzadeh et al.

It is certified that error appears in the above-identified patent and that said Letters Patent is hereby corrected as shown below:

In the Specification

In Column 2, Line 14 please delete "WV" and replace it with --UV--.

In Column 7, Line 58 please delete "anti-inflamatory" and replace it with --anti-inflammatory--.

Signed and Sealed this
Fifth Day of June, 2018

Andrei Iancu
*Director of the United States Patent and Trademark Office*